(12) United States Patent
Moriyama et al.

(10) Patent No.: US 10,619,181 B2
(45) Date of Patent: Apr. 14, 2020

(54) **METHOD FOR DETECTING A *SHIGELLA* OR *CRONOBACTER* MICROORGANISM**

(71) Applicant: 3M INNOVATIVE PROPERTIES COMPANY, St. Paul, MN (US)

(72) Inventors: Takatoshi Moriyama, Kanagawa (JP); Patrick A. Mach, Shorewood, MN (US); Akio Kitahara, Kanagawa (JP); Henry J. Lubrant, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 9 days.

(21) Appl. No.: 16/035,758

(22) Filed: Jul. 16, 2018

(65) Prior Publication Data

US 2018/0320213 A1 Nov. 8, 2018

Related U.S. Application Data

(60) Continuation of application No. 15/628,750, filed on Jun. 21, 2017, now Pat. No. 10,023,898, which is a continuation of application No. 14/956,437, filed on Dec. 2, 2015, now Pat. No. 9,719,124, which is a division of application No. 13/976,064, filed as application No. PCT/US2011/067149 on Dec. 23, 2011, now Pat. No. 9,273,340.

(60) Provisional application No. 61/428,722, filed on Dec. 30, 2010.

(51) Int. Cl.
| | |
|---|---|
| *C12Q 1/10* | (2006.01) |
| *C12Q 1/04* | (2006.01) |
| *C12Q 1/34* | (2006.01) |
| *C12Q 1/44* | (2006.01) |

(52) U.S. Cl.
CPC ............ *C12Q 1/04* (2013.01); *C12Q 1/10* (2013.01); *C12Q 1/34* (2013.01); *C12Q 1/44* (2013.01)

(58) Field of Classification Search
None
See application file for complete search history.

(56) References Cited

U.S. PATENT DOCUMENTS

| | | |
|---|---|---|
| 4,279,995 A | 7/1981 | Woods et al. |
| 4,565,783 A | 1/1986 | Hansen et al. |
| 5,194,374 A | 3/1993 | Rambach |
| 5,385,826 A | 1/1995 | Schell et al. |
| 5,434,056 A | 7/1995 | Monget et al. |
| 5,629,170 A | 5/1997 | Mondello |
| 5,786,167 A | 7/1998 | Tuompo et al. |
| 5,888,760 A | 3/1999 | Godsey et al. |
| 6,022,682 A | 2/2000 | Mach et al. |
| 6,068,988 A | 5/2000 | Schabert et al. |
| 6,228,606 B1 | 5/2001 | Facon et al. |
| 6,368,817 B1 | 4/2002 | Perry et al. |
| 6,617,149 B2 | 9/2003 | Restaino |
| 7,150,977 B2 | 12/2006 | Restaino |
| 7,351,548 B2 | 4/2008 | Rambach |
| 9,273,340 B2 * | 3/2016 | Moriyama ............... C12Q 1/04 |
| 9,677,111 B2 | 6/2017 | Binsfeld et al. |
| 9,719,124 B2 * | 8/2017 | Moriyama ............... C12Q 1/04 |
| 10,023,898 B2 * | 7/2018 | Moriyama ............... C12Q 1/04 |
| 2002/0058298 A1 | 5/2002 | Townsend |
| 2006/0257967 A1 | 11/2006 | Restaino |
| 2007/0259393 A1 | 11/2007 | Restaino |
| 2008/0096195 A1 | 4/2008 | Rambach |
| 2010/0240091 A1 | 9/2010 | Blanc et al. |
| 2012/0094327 A1 | 4/2012 | Young et al. |

FOREIGN PATENT DOCUMENTS

| | | |
|---|---|---|
| EP | 0 454 046 | 10/1991 |
| JP | S60-248165 | 12/1985 |
| JP | 4-147063 | 5/1992 |
| JP | 2001-321196 | 11/2001 |
| JP | 2004-57054 | 2/2004 |
| JP | 2004-187588 | 7/2004 |
| JP | 2008-017712 | 1/2008 |
| WO | 1999/18232 | 4/1999 |
| WO | 2007/023185 | 3/2007 |
| WO | 2009/056762 | 5/2009 |

OTHER PUBLICATIONS

George, I. et al.; "Use of rapid enzymatic assays to study the distribution of faecal coliforms in the Seine river (France)"; Water Science and Technology; vol. 43, No. 12; 2001; pp. 77-80.

Shadix L. et al.; "Evaluation of β-glucuronidase assay for the detection of *Escherichia coli* from environmental waters"; Canadian J. of Microbiology; vol. 37, No. 12; 1991; pp. 908-911.

Leimeister-Wachter, M. et al.; "Detection of a gene encoding a phosphatidylinositol-specific phospholipase C that is co-ordinately expressed with listeriolysin in *Listeria* monocytogenes"; Molecular Microbiology; vol. 5, No. 2; 1991; pp. 361-366.

* cited by examiner

*Primary Examiner* — Ralph J Gitomer
(74) *Attorney, Agent, or Firm* — Eric E. Silverman (57) ABSTRACT

A method of detecting a *Shigella* or *Cronobacter* microorganism. The method comprises providing a culture device with a selective culture medium and a detection article comprising a first indicator system.

13 Claims, 3 Drawing Sheets

METHOD FOR DETECTING A *SHIGELLA* OR *CRONOBACTER* MICROORGANISM

CROSS REFERENCE TO RELATED APPLICATIONS

This application is a continuation of Ser. No. 15/628,750, filed Jun. 21, 2017, now allowed, which is a continuation of U.S. patent application Ser. No. 14/956,437, filed Dec. 2, 2015, now U.S. Pat. No. 9,719,124, which is a division of U.S. patent application Ser. No. 13/976,064, filed Jun. 26, 2013, now U.S. Pat. No. 9,273,340, which is a National Stage application filed under 35 U.S.C. 371 based on PCT/US2011/067149, filed 23 Dec. 2011, which claims the benefit of U.S. Provisional Patent Application No. 61/428,722, filed Dec. 30, 2010, all of which are incorporated herein by reference in their entirety.

BACKGROUND

Testing samples of all food, beverages, and water for pathogenic microorganisms may not be practical because of the expense and because pathogenic microorganisms are rarely found in, for example, properly-processed food. Therefore, tests for the presence of indicator microorganisms are routinely used to test food and water to determine the likelihood of contamination with human pathogens. The presence of one or more indicator microorganisms can be an indication of fecal contamination, for example, and may indicate the potential presence of a pathogenic microorganism.

Coliform bacteria ("coliforms") represent one example of indicator microorganisms. The coliform group includes a number of genera (e.g., *Citrobacter, Enterobacter, Escherichia, Hafnia, Klebsiella*, and *Serratia*) of rod-shaped Gram-negative bacteria that are found in large numbers in the feces of warm-blooded animals and are characterized by their ability to ferment lactose to acid and gas by-products. Although most coliforms are only associated with opportunistic infections in humans, some coliform bacteria (e.g., *E. coli* O157:H7 or other Shiga Toxin producing *E. coli*—STEC) are associated with a higher incidence of morbidity and mortality.

Members of the Enterobacteriaceae family of microorganisms represent another example of indicator microorganisms. In addition to the coliform bacteria, this family also includes a large number of other rod-shaped Gram-negative bacteria. Like coliform bacteria, the presence of Enterobacteriaceae microorganisms in a food or water sample can indicate the presence of fecal contamination and, thus, the possible presence of human pathogens (e.g., *Salmonella enterica* Enteritidis, *Salmonella enterica* Typhimurium, *Shigella* species, and *Cronobacter* species).

There is a need for efficient methods to test for the presence of pathogenic microorganisms in a sample.

SUMMARY

In general, the invention is directed to a method for assessing the microbiological content of a sample (e.g., a sample of food or water, an environmental sample). In particular, the inventive method can detect the presence or absence of a target microorganism in a sample that has been found to contain an indicator organism that can indicate the presence of the target microorganism. The inventive method includes culturing a sample in a culture device with a first indicator system to determine the presence of an indicator microorganism and, if an indicator microorganism is detected, contacting the culture device with a detection article comprising a second indicator system to determine the presence or absence of a target microorganism.

In one aspect, the present disclosure provides a method of detecting the presence or absence of a target microorganism. The method can comprise providing a culture device including a culture medium comprising ingredients selected to facilitate growth of a predetermined indicator microorganism, a detection article comprising a first indicator system, and a sample. The first indicator system can be selected to detect a target microorganism. The method further can comprise, inoculating the culture device with the sample, incubating the inoculated culture device for a period of time sufficient to permit growth of the indicator microorganisms, observing the culture device for an indication of a presence of at least one indicator microorganism, contacting the culture medium of the incubated culture device with the detection article, and observing the article-contacted culture device to detect a conversion of the first indicator system from a first state to a second state. In some embodiments, the conversion of the first indicator system from a first state to a second state, if present, can be indicative of the presence of at least one target microorganism. In some embodiments, the conversion of the first indicator system from a first state to a second state, if absent, is indicative of the presence of at least one target microorganism.

In some embodiments, the method further can comprise providing a second indicator system and placing the second indicator system in fluid communication with the culture medium, wherein observing the culture device for a presence of at least one indicator microorganism comprises detecting a presence or absence of a conversion of the second indicator system from a first state to a second state. In any of the above embodiments, providing a culture device further can comprise providing a culture device that includes the second indicator system. In any of the above embodiments of the method, providing the culture device further can comprise providing a culture device that comprises a hydrogel or a dry, cold-water-soluble gelling agent.

In any of the above embodiments of the method, contacting the culture medium with the detection article is performed only when the indication of the presence of at least one indicator microorganism is observed.

In any of the above embodiments, providing a culture medium can comprise providing a culture medium selected to facilitate growth of an Enterobacteriaceae microorganism, wherein providing a detection article can comprise providing a detection article to detect a microorganism of the genus *Salmonella*. In some embodiments, the first indicator system can comprise a reagent to detect α-galactosidase or caprylate esterase enzyme activity.

In any of the above embodiments, providing a culture medium can comprise providing a culture medium selected to facilitate growth of an Enterobacteriaceae microorganism, wherein providing a detection article can comprise providing a detection article to detect a microorganism of the genus *Shigella*. In some embodiments, the first indicator system can comprise a reagent to detect β-glucosidase, β-fucosidase, N-acetyl-β-galactosaminidase, or a combination of any two or more of the foregoing enzyme activities.

In any of the above embodiments, providing a culture medium can comprise providing a culture medium selected to facilitate growth of an Enterobacteriaceae microorganism, wherein providing a detection article can comprise providing a detection article to detect a microorganism of the genus *Cronobacter*. In some embodiments, the first indicator system can comprise a reagent to detect α-glucosidase and/or β-cellobiosidase enzyme activity.

In any of the above embodiments, providing a culture medium can comprise providing a culture medium selected to facilitate growth of an Enterobacteriaceae microorganism, wherein providing a detection article can comprise providing a detection article to detect *Escherichia coli*. In any of the above embodiments, providing a culture medium comprises providing a culture medium selected to facilitate growth of a coliform microorganism, wherein providing a detection article comprises providing a detection article to detect *Escherichia coli*. In some embodiments, the first indicator system can comprise a reagent to detect β-glucuronidase enzyme activity.

In some embodiments, providing a culture medium can comprise providing a culture medium selected to facilitate growth of a microorganisms of the *Listeria* genus, wherein providing a detection article can comprise providing a detection article to detect *Listeria monocytogenes*. In some embodiments, the first indicator system can comprise a reagent to detect α-mannopyranosidase or phosphatidylinositol-specific phospholipase C enzyme activity.

In any of the above embodiments, observing the culture device or the article-contacted culture device can comprise observing the culture device visually. In any of the above embodiments, observing the culture device or the article-contacted culture device can comprise observing the culture device using an automated reader. In any of the above embodiments, the method further can comprise enumerating a portion of indicator microorganism colony-forming units. In any of the above embodiments, the method further can comprise enumerating a portion of target microorganism colony-forming units.

In any of the above embodiments, contacting the culture medium with the detection article further can comprise contacting the culture medium at a predetermined temperature.

In another aspect, the present disclosure provides an article. The article can comprise a substrate with upper and lower major surfaces and a coating disposed on at least one of the major surfaces. The coating can comprise a first indicator system. The indicator system can be converted from a first state to a second state by α-galactopyranoside or caprylate esterase enzyme activity. In some embodiments of the article, the first indicator system can be selected from the group consisting of 5-bromo-4-chloro-3-indolyl-α-D-galactopyranoside, 5-bromo-6-chloro-3-indolyl-caprylic acid, and 5-bromo-4-chloro-3-indolyl-caprylic acid.

In yet another aspect, the present disclosure provides an article. The article can comprise a substrate with upper and lower major surfaces and a coating disposed on at least one of the major surfaces. The coating can comprise a first indicator system. The first indicator system can be converted from a first state to a second state by β-glucuronidase enzyme activity. In some embodiments, the first indicator system can be selected from the group consisting of 5-bromo-4-chloro-3-indolyl-β-D-glucuronic acid, p-nitrophenyl-β-glucuronide, p-nitrophenyl-2,3,4-tri-O-acetyl-β-glucuronic acid methyl ester, phenolphthalein glucuronic acid, phenolphthalein mono-P-glucuronic acid, naphthyl-AS-BI-β-D-glucuronide, and 4-methylumbelliferyl β-D-glucuronide, 8-Hydroxyquinoline-beta-D-glucuronic acid, sodium salt, 2-Naphthyl-beta-D-glucuronic acid, sodium salt, 4-Nitrophenyl-beta-D-glucuronic acid, sodium salt, Phenolphthalein-beta-D-glucuronic acid, sodium salt monohydrate. 5-Bromo-4-chloro-3-indoxyl-beta-D-glucuronic acid, cyclohexylammonium salt, 3-Indoxyl-beta-D-glucuronic acid, cyclohexylammonium salt, 3-Indoxyl-beta-D-glucuronic acid, sodium salt, 5-Bromo-6-chloro-3-indoxyl-beta-D-glucuronic acid, cyclohexylammonium salt, 5-Bromo-4-chloro-3-indoxyl-beta-D-glucuronic acid, sodium salt anhydrous, and 5-Bromo-4-chloro-3-indoxyl-beta-D-glucuronic acid, sodium salt trihydrate.

In yet another aspect, the present disclosure provides an article. The article can comprise a substrate with upper and lower major surfaces and a coating disposed on at least one of the major surfaces. The coating can comprise a first indicator system. The first indicator system can be converted from a first state to a second state by α-mannopyranosidase or phosphatidylinositol-specific phospholipase C enzyme activity. In some embodiments, the first indicator system can be selected from the group consisting of 5-bromo-4-chloro-3-indoxyl-myo-inositol-1-phosphate, 5-Bromo-6-chloro-3-indoxyl myo-inositol-1-phosphate, ammonium salt, 4-Methylumbelliferyl myo-inositol-1-phosphate, N-methylmorpholine salt,3-indoxyl-α-D-mannopyranoside, 5-bromo-3-indoxyl-α-D-mannopyranoside, 4-chloro-3-indoxyl-α-D-mannopyranoside, 5-iodo-3-indoxyl-α-D-mannopyranoside, 5-bromo-4-chloro-3-indoxyl-α-D-mannopyranoside, chloro-3-indoxyl-α-D-mannopyranoside, 5-bromo-6-chloro-3-indoxyl-α-D-mannopyranoside, 6-bromo-3-indoxyl-α-D-mannopyranoside, 6-chloro-3-indoxyl-α-D-mannopyranoside, 6-fluoro-3-indoxyl-α-D-mannopyranoside, 4,6-dichloro-3-indoxyl-α-D-mannopyranoside, 6,7-dichloro-3-indoxyl-α-D-mannopyranoside, 4,6,7-trichloro-3-indoxyl-α-D-mannopyranoside, 5-bromo-4-chloro-N-methyl-α-D-mannopyranoside, 3-indoxyl-α-D-mannopyranoside, and N-methyl-3-indoxy-α-D-mannopyranoside, 6-Bromo-2-naphthyl-α-D-mannopyranoside, 4-Methylumbelliferyl-α-D-mannopyranoside, and 4-Nitrophenyl-α-D-mannopyranoside.

In any of the above embodiments, the coating can be disposed on the upper and lower major surfaces. In any of the above embodiments, the article further can comprise an adhesive layer. In some embodiments, at least a portion of the first indicator system can be disposed on or in the adhesive layer. In any of the above embodiments, the first indicator system can be disposed on both major surfaces. In any of the above embodiments, the substrate can be selected from the group consisting of a polymeric film, paper, a nonwoven, a membrane filter and derivatives of any of the foregoing. In any of the above embodiments, the coating further can comprise a binder.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a microorganism can be interpreted to mean "one or more" microorganisms.

The term "and/or" means one or all of the listed elements or a combination of any two or more of the listed elements.

"Culture device", as used herein, refers to an article adapted to house a nutrient medium that facilitates the growth of a microorganism. Optionally, the culture device may comprise a lid or cover to minimize the exposure of the nutrient medium to external contamination and/or to reduce the loss of moisture from the culture medium during incubation and/or storage. Nonlimiting examples of culture devices include flasks, beakers, tubes, Petri dishes, multi-well plates, PETRIFILM plates, COMPACT DRY media sheets, SANITA-KUN sheets, and the like.

"Indicator system", as used herein, refers to one or more of any of the following and any combination of one or more of the following: a chromogenic enzyme substrate, a fluorogenic enzyme substrate, a redox indicator (e.g., triphenyltetrazolium chloride, methylene blue), a metabolizable nutrient, pH indicator. "Metabolizable nutrient" refers to any molecule that can be used by a predetermined indicator organism and/or a predetermined target microorganism to produce biomass and/or energy. The use of the metabolizable nutrient by the microorganisms directly or indirectly results in a pH or other detectable ionic change in an aqueous medium that is in fluid contact with the microorganism. A "differentiating" indicator system is an indicator system that can be used to distinguish two nonidentical microorganisms based on their respective reactivities with a component(s) of the indicator system(s).

"Indicator microorganism", as used herein, refers to a microorganism that belongs to a group of microorganisms that is known to be found in an environment (e.g. a liquid or solid matrix) in which a target microorganism is also found. According to the present disclosure, indicator microorganisms and their corresponding target microorganisms are capable of being cultured in the same culture medium. In addition, target microorganisms may react with the same indicator system that detects the corresponding indicator microorganisms. Indicator microorganisms can include relatively large and diverse groups of microorganisms (e.g., aerobic bacteria, yeast, filamentous fungi), relatively large and relatively less diverse groups of microorganisms (e.g., a phylogenetically-related group of microorganisms such as the Enterobacteriaceae family, for example, or a physiologically-related group of microorganisms such as the coliform bacteria, for example), and even smaller groups and/or relatively less diverse groups of microorganisms (e.g., a genus such as *Listeria*, a species such as *Escherichia coli*).

"Target microorganism", as used herein, refers a predetermined microorganism that can be found in one or more of the same environments that the indicator microorganisms are found. A target microorganism can be distinguished from one or more of a group of indicator microorganisms on the basis of its reactivity, or lack thereof, with a differentiating indicator system. In some embodiments, the target microorganism can belong to the group of indicator microorganisms (e.g., an exemplary target microorganism, *Escherichia coli*, is a member of the Enterobacteriaceae family, which is a group of indicator microorganisms known in the art). In certain embodiments, "target microorganism" may refer to one or more strains of a particular species, one or more species of a particular genus, or more than one species from each of two or more genera or one or more strains or species of a non-taxonomic (e.g., physiologically-related) group.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

The invention is directed to a method for assessing the microbiological content of a sample. In particular, the method includes sequential detection processes that, advantageously, are conducted in a single culture device. The detection processes are distinct, but related in the sense that the first detection process identifies a group of indicator microorganisms and the second detection process identifies a target microorganism within the group. Advantageously, the result of the first identification process can be used to decide whether the use of the second detection process is indicated. Accordingly, in some embodiments, when an indicator microorganism is not detected by the first identification process, an operator can avoid the time, materials, labor, and expense of the second identification process.

Figure 1:
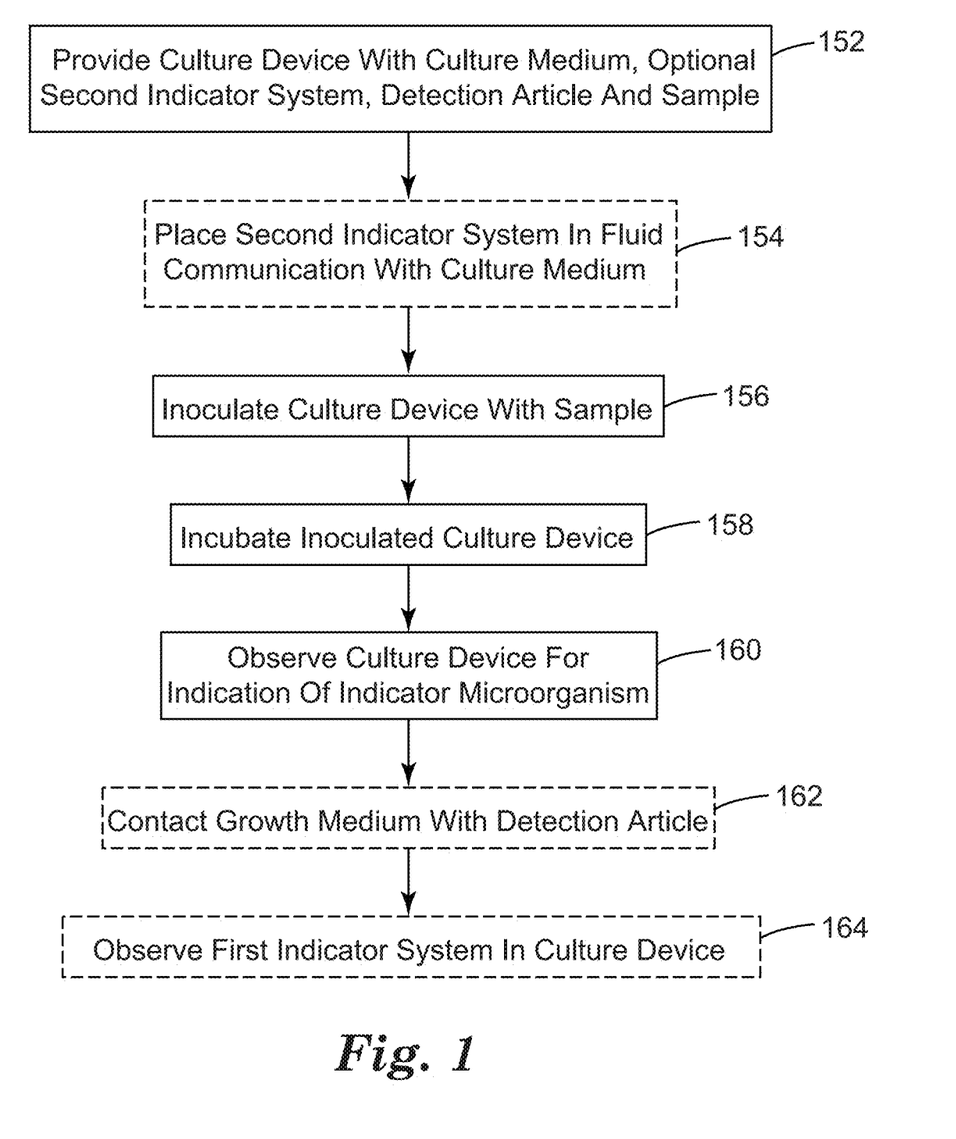
FIG. 1 is a block diagram of one embodiment of a method for detecting a target microorganism according to the present disclosure.

FIG. 1 is a block diagram showing one embodiment of a method of detecting a target microorganism according to the present disclosure. Methods of the present disclosure are directed to testing a sample for the presence or absence of a target microorganism. The method includes the step 152 of providing a sample to be tested, a detection article, and a culture device that includes a culture medium. Optionally, a second indicator system can be provided. The method further comprises the step 154 of placing the second indicator system, if present, in fluid communication with the culture medium. The method further comprises the step 156 of inoculating the culture device with the sample, the step 158 of incubating the inoculated culture device, and the step 160 of observing the culture device for an indication of an indicator microorganism. If an indicator microorganism is observed in step 160, the method further comprises the optional step 162 of contacting the culture medium with the detection article and the step 164 of observing the first indicator system. Each of the steps in the method is described in greater detail below. An advantage of the method is that the detection article may only need to be applied to the culture medium if an indication of an indicator microorganism is detected. Thus, in samples where no indication of an indicator microorganism is detected, it may be inferred that a target microorganism is not present and the detection article does not have to be used.

Providing a sample to be tested may comprise providing a sample that is suspected of containing a target microorganism. The sample can be any sample that may include a target microorganism as defined herein. Nonlimiting examples of suitable samples include environmental samples (e.g., surface swabs/sponges, soil, sediments, fomites), food (e.g., raw materials, in-process samples, and finished-product samples), beverages, clinical/veterinary samples (e.g., blood, serum, plasma, urine, sputum, tissue, mucous, feces, wound exudate, pus, cerebrospinal fluid), and water (e.g., surface water, potable water, process water).

In some embodiments, the presence or absence of a target microorganism can be analyzed in a test sample that is derived from a variety of food, beverage, or food- or beverage-processing environmental sources. Non-limiting examples of food sources include raw or processed meat, raw or processed fruits or vegetables, non-fluid dairy products (e.g., cheese, butter, and ice cream), nuts, spices, ingredients, and syrups. Non-limiting examples of beverage sources include potable water, fruit or vegetable juices, milk, and fermented beverages. Pasteurized food or beverages may also be suitable sources. Non-limiting examples of food- or beverage-processing environmental samples include food-handling surface samples (e.g., conveyor belts, blades, cutting surfaces, mixing equipment surfaces, filters, storage containers), room samples (e.g., walls, floors, drains, ventilation equipment), and cleaning equipment (e.g., hoses, cleaning tools).

In some embodiments, the presence or absence of a target microorganism can be analyzed in a sample that is derived from a variety of human or animal sources, such as a physiological fluid, e.g., blood, saliva, ocular lens fluid, synovial fluid, cerebral spinal fluid, pus, sweat, exudate, urine, mucus, lactation milk, or the like. Further, the test sample may be derived from a body site, e.g., wound, skin, nares, scalp, nails, etc.

Samples of particular interest from human or animal sources include mucus-containing samples, such as nasal samples (from, e.g., anterial nares, nasopharyngeal cavity, nasal cavities, anterior nasal vestibule, etc.), as well as samples from the outer ear, middle ear, mouth, rectum, vagina, or other similar tissue. Examples of specific mocusal tissues include buccal, gingival, nasal, ocular, tracheal, bronchial, gastrointestinal, rectal, urethral, ureteral, vaginal, cervical, and uterine mucosal membranes.

Besides physiological fluids, other test samples may include other liquids as well as solid(s) dissolved in a liquid medium. Samples of interest may include process streams, water, soil, plants or other vegetation, air, surfaces (e.g., contaminated surfaces), and the like. Samples can also include cultured cells. Samples can also include samples on or in a device comprising cells, spores, or enzymes (e.g., a biological indicator device).

Suitable samples for methods of the present disclosure can include certain solid samples. Solid samples may be disintegrated (e.g., by blending, sonication, homogenization) and may be suspended in a liquid (e.g., water, buffer, broth). In some embodiments, a sample-collection device (e.g., a swab, a sponge) containing sample material may be used in the method. Alternatively, the sample material may be eluted (e.g., rinsed, scraped, expressed) from the sample-collection device before using the sample material in the method. In some embodiments, liquid or solid samples may be diluted in a liquid (e.g., water, buffer, broth).

The sample may comprise an indicator microorganism, as described herein. The indicator microorganism can be indicative of contamination (e.g., fecal contamination), infection (e.g., infection with a pathogenic microorganism), or an indicator of general sanitation (e.g., any aerobic microorganism). The indicator microorganism further can be a target microorganism.

Microorganisms of particular interest, which may be of interest as an indicator organism or a target microorganism, include prokaryotic and eukaryotic organisms, particularly Gram positive bacteria, Gram negative bacteria, fungi, *mycoplasma*, and yeast. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Listeria* spp., *Vibrio* spp., *Corynebacteria* spp. as well as herpes virus, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis*, *Streptococcus pneumoniae*, *S. agalactiae*, *S. pyogenes*, *Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracis*, *Pseudomonas aeruginosa*, *Escherichia coli*, *Aspergillus niger*, *A. fumigatus*, *A. clavatus*, *Fusarium solani*, *F. oxysporum*, *F. chlamydosporum*, *Listeria monocytogenes*, *Listeria ivanovii*, *Vibrio cholera*, *V parahaemolyticus*, *Salmonella choleraesuis*, *S. typhi*, *S. typhimurium*, *Candida albicans*, *C. glabrata*, *C. krusei*, *Cronobacter sakazakii*, *E. coli* O157 and multiple drug resistant Gram negative rods (MDR).

Gram positive and Gram negative bacteria are of particular interest. Of particular interest are Gram positive bacteria, such as *Listeria monocytogenes*. Also, of particular interest are antibiotic resistant microbes including MRSA, VRSA, VISA, VRE, and MDR microbes.

Referring back to step 152 of FIG. 1, in addition to providing a sample to be tested, the method further includes providing a culture device, a first indicator system, and an article with a second indicator system coated thereon. Culture device is used in a broad sense and includes a variety of articles adapted to house a nutrient medium that facilitates the growth of a microorganism. The selection of a particular nutrient medium to facilitate the growth of any particular indicator microorganism according to the method is within the grasp of a person having ordinary skill in the art.

In some embodiments, the nutrient medium can comprise one or more selective inhibitors. "Selective inhibitors", as used herein, refers to chemical compounds that are added to nutrient medium to partially or completely inhibit the growth of certain susceptible microorganisms or groups of microorganisms, thereby selectively favoring the growth of other microorganisms or groups of microorganisms. Selective inhibitors are known in the art and include, for example, bile salts, inorganic salts (e.g., NaCl, LiCl, $MgCl_2$), and antibiotics (fluoroquinolones, β-lactam antibiotics, aminoglycosides). In certain preferred embodiments of the present disclosure, the nutrient medium can include selective inhibitors at concentrations that are minimally-selective (i.e., at concentrations that are below the customary concentrations used in selective growth media). Advantageously, the use of minimally-selective nutrient medium can permit the recovery and detection of more target microorganisms using the method of the present disclosure. Without being bound by theory, this may be possible because the lower concentration of selective inhibitors permit the growth of injured, stressed, and/or relatively-susceptible target microorganisms in the selective medium, thereby enabling their detection with the second indicator system.

The first indicator system is used to indicate the presence or absence of a target microorganism. The optional second indicator system is used to indicate the presence or absence of an indicator microorganism. The first and/or second indicator system can comprise a chromogenic enzyme substrate, a fluorogenic enzyme substrate, a redox indicator, a metabolizable nutrient, a pH indicator, or any combination of two or more of the foregoing. In some embodiments, the combination of a pH indicator and a certain metabolizable nutrient may be provided for the method by providing one of the components in the culture medium of the culture device and by providing the other component in the detection article.

The choice of the first indicator system may depend upon the target microorganism and/or the culture medium used in the culture device and such choices are guided by the present disclosure, as will be recognized by a person having ordinary skill in the art. In some embodiments of the method, a highly-differential first indicator system (i.e., an indicator system that reacts with relatively few microorganisms, including the target microorganism) can be used in conjunction with a minimally selective culture medium. In these embodiments, the minimally-selective culture medium can permit the recovery and growth of injured and/or stressed target microorganisms, thereby enabling the detection of such target organisms that may be inhibited by a relatively highly-selective culture medium.

In some embodiments of the method, a relatively less-differential first indicator system (i.e., an indicator system that reacts with relatively many microorganisms, including the target microorganism) can be used in conjunction with a relatively highly-selective culture medium. This approach may be used with highly complex samples (e.g., samples that require strongly-selective conditions such as samples from floor drains that tend to have large-highly diverse microbial contents or samples from relatively non-selective pre-enrichment broth cultures). An example of this approach is the use of the Demi-Fraser/UVM, Fraser broth enrichment system with Modified Oxford agar detection of *Listeria* microorganisms.

In any of the embodiments, the first or second indicator system can comprise an oxidation-reduction indicator (also called a redox indicator) suitable to biological oxidation-reduction reactions. Oxidation-reduction indicator dyes may be pH-dependent or pH-independent. Nonlimiting examples of oxidation-reduction indicator dyes include 2,2'-Bipyridine (Ru complex), Nitrophenanthroline (Fe complex), N-Phenylanthranilic acid, 1,10-Phenanthroline (Fe complex), N-Ethoxychrysoidine, 2,2'-Bipyridine (Fe complex), 5,6-Dimethylphenanthroline (Fe complex), o-Dianisidine, Sodium diphenylamine sulfonate, Diphenylbenzidine, Diphenylamine, Viologen, Sodium 2,6-Dibromophenol-indophenol, Sodium 2,6-Dichlorophenol-indophenol, Sodium o-Cresol indophenol, Thionine (syn. Lauth's violet), Methylene blue, Indigotetrasulfonic acid, Indigotrisulfonic acid, Indigodisulfonic acid, Indigomonosulfonic acid, Phenosafranin, Safranin T, and Neutral red.

In any of the embodiments, the first and/or second indicator system can comprise a chromogenic enzyme substrate. Eligible chromogenic enzyme substrates include bromo-chloro-indolyl derivatives, nitrophenyl derivatives, and phenolphthalein derivatives, for example.

Useful 5-bromo-4-chloro-3-indolyl derivatives include 5-bromo-6-chloro-3-indolyl acetate, 5-bromo-4-chloro-3-indolyl acetate, 5-bromo-4-chloro-3-indoxyl-β-D-galactopyranoside, 5-bromo-4-chloro-3-indoyl-1,3diacetate, 5-bromo-4-chloro-3-indolyl-β-D-fucopyranoside, 5-bromo-4-chloro-3-indolyl-β-D-glucopyranoside, 5-bromo-4-chloro-3-indolyl-β-D-glucuronic acid, 5-bromo-4-chloro-3-indolyl phosphate, and 5-bromo-4-chloro-3-indolyl sulfate.

Useful nitrophenyl derivatives include p-nitrophenol and o-nitrophenol derivatives. Particularly useful p-nitrophenols include diethyl-p-nitrophenyl phosphate; di-p-nitrophenyl phosphate; p-nitrophenyl-2-acetamido-2-deoxy-3-O-β-galactopyranosyl-β-glucopyranoside; p-nitrophenyl-2-acetamido-2-deoxy-β-glucopyranoside; p-nitrophenylacetate, p-nitrophenyl-N-acetyl-β-D-glucosaminide, p-nitrophenyl-β-D-N,N'-diacetylchitobioside; p-nitrophenyl-α-glucopyranoside, p-nitrophenyl-α-maltoside; p-nitrophenyl-β-maltoside; p-nitrophenyl-α-mannopyranoside; p-nitrophenyl-β-mannopyranoside; p-nitrophenyl myristate; p-nitrophenyl palmitate; p-nitrophenyl phosphate; bis(p-nitrophenyl)phosphate; tris(p-nitrophenyl)phosphate; p-nitrophenyl-β-glucopyranoside; p-nitrophenyl-β-glucuronide; α-p-nitrophenylglycerine; p-nitrophenyl-α-rhamnopyranoside; p-nitrophenyl stearate; p-nitrophenyl sulfate; p-nitrophenyl-2,3,4-tri-O-acetyl-β-glucuronic acid methyl ester; and p-nitrophenyl valerate.

Particularly useful o-nitrophenols include o-nitrophenyl acetate, o-nitrophenyl-β-glucoside and o-nitrophenyl-β-D-glucopyranoside. Other particularly useful nitrophenyl derivatives include nitrophenyl-β-fucopyranoside, nitrophenyl-α-galactopyranoside, nitrophenyl butyrate, nitrophenyl caprate, nitrophenyl caproate, nitrophenyl caprylate, nitrophenyl laurate, and nitrophenyl propionate.

Useful indoxyl derivatives include indoxyl-acetate; indoxyl β-D-glucoside; 3-indoxyl sulfate; 3-indoxy 1 phosphate.

Useful phenolphthalein derivatives include: phenolphthalein dibutyrate; phenolphthalein diphosphate; phenolphthalein disulfate; phenolphthalein glucuronic acid; phenolphthalein mono-P-glucosiduronic acid; phenolphthalein mono-P-glucuronic acid; and phenolphthalein monophosphate.

All of the above-described chromogenic substrates will react directly with an appropriate enzyme to produce a chromophore.

Additional enzyme substrates containing 1-naphthyl, 2-naphthyl and Naphthyl-AS-BI derivatives are usefully employed if the derivative enzyme modified product is further reacted with a chromogenic reagent, such as diazotized dyes, e.g., 1-diazo-4-benzoylamino-2,5,diethoxybenzene, (commercially available as "Fast Blue BB Salt" from Sigma Chemical), 1-diazo-4-benzoylamino-2,5-diethoxybenzene, p-diazo-2,5-diethoxy-N-benzoylalanine, chloro-2-methylbenzene diazonium chloride, and o-aminoazotoluene diazonium salt, to produce a chromophore.

Particularly useful 1-naphthyl derivatives include 1-naphthyl-N-acetyl-β-D-glucosaminide.

Particularly useful 2-naphthyl derivatives include 2-naphthyl-phosphate; 2-naphthyl-butyrate; 2-naphthyl-caprylate; 2-naphthyl-myristate; L-leucyl-2-naphthylamide; L-valyl-2-naphthylamide; L-cystyl-2-naphthylamide; N-benzoyl-DL-arginine-2-naphthylamide; N-glutarylphenylalanine-2-naphthylamine; 2-naphthyl-phosphate; 6-Br-2-naphthyl-α-D-galactopyranoside; 2-naphthyl-β-D-galactopyranoside; 2-naphthyl-2-D-glucopyranoside; 6-bromo-2-naphthol-β-D-glucopyranoside; 6-bromo-2-naphthyl-2-D-mannopyranoside; and 2-naphthyl-α-L-fucopyranoside.

Particularly useful naphthyl-AS-BI derivatives include naphthyl-AS-BI-phosphate and naphthyl-AS-BI-β-D-glucuronide.

Where the enzyme whose activity is to be detected is alpha-D-glucosidase, a suitable chromogenic enzyme substrate, for example, is p-nitrophenyl-α-glucopyranoside. Where the enzyme activity to be detected is alpha-L-arabinofuranosidase, a suitable chromogenic enzyme substrate, for example, is p-nitrophenyl-α-L-arabinofuranoside. Where the enzyme activity to be detected is beta-D-glucosidase, a suitable chromogenic enzyme substrate, for example, is p-nitrophenyl-β-D-glucopyranoside.

In any of the embodiments, the first and/or second indicator system can comprise a fluorogenic enzyme substrate. Eligible fluorogenic enzyme substrates include derivatives of 4-methylumbelliferone 7-amido-4-methylcoumarin, fluorescein, rhodamine, and fluorescamine, for example.

Suitable 4-methylumbelliferyl derivatives include, for example: 4-methylumbelliferyl-2-acetamido-4,6-O-benzylidene-2-deoxy-β-D-glucopyranoside; 4-methylumbelliferyl acetate; 4-methylumbelliferyl-N-acetyl-β-D-galactosaminide; 4-methylumbelliferyl-N-acetyl-α-D-glucosaminide; 4-methylumbelliferyl-N-acetyl-β-D-glucosaminide; 2'-(4-methylumbelliferyl)-α-D-N-acetyl neuraminic acid; 4-methylumbelliferyl α-L-arabinofuranoside; 4-methylumbelliferyl α-L-arabinoside; 4-methylumbelliferyl butyrate; 4-methylumbelliferyl β-D-cellobioside; methylumbelliferyl β-D-N, N'diacetylchitobioside; 4-methylumbelliferyl elaidate; 4-methylumbelliferyl β-D-fucoside; 4-methylumbelliferyl α-L-fucoside; 4-methylumbelliferyl β-L-fucoside; 4-methylumbelliferyl α-D-galactoside; 4-methylumbelliferyl β-D-galactoside; 4-methylumbelliferyl α-D-glucoside; 4-methylumbelliferyl β-D-glucoside; 4-methylumbelliferyl β-D-glucuronide; 4-methylumbelliferyl p-guanidinobenzoate; 4-methylumbelliferyl heptanoate; 4-methylumbelliferyl α-D-mannopyranoside; 4-methylumbelliferyl β-D-mannopyranoside; 4-methylumbelliferyl oleate; 4-methylumbelliferyl palmitate; 4-methylumbelliferyl phosphate; 4-methylumbelliferyl propionate; 4-methylumbelliferyl stearate; 4-methylumbelliferyl sulfate; 4-methylumbelliferyl β-D-N, N', N"-triacetylchitotriose; 4-methylumbelliferyl 2,3,5-tri-o-benzoyl-α-L-arabinofuranoside; 4-methylumbelliferyl-p-trimethylammonium cinnamate chloride; and 4-methylumbelliferyl β-D-xyloside.

Suitable 7-amido-4-methylcoumarin derivatives include, for example: L-alanine-7-amido-4-methylcoumarin; L-proline 7-amido-4-methylcoumarin; L-tyrosine-7-amido-4-methylcoumarin; L-leucine-7-amido-4-methylcoumarin; L-phenylalanine-7-amido-4-methylcoumarin; and 7-glutarylphenylalanine-7-amido-4-methylcoumarin.

Suitable peptide derivatives of 7-amido-4-methyl coumarin include, for example: N-t-BOC-Ile-Glu-Gly-Arg 7-amido-4-methylcoumarin; N-t-BOC-Leu-Ser-Thr-Arg 7-amido-4-methylcoumarin; N-CBZ-Phe-Arg 7-amido-4-methyl-coumarin; Pro-Phe-Arg 7-amido-4-methylcoumarin; N-t-BOC-Val-Pro-Arg 7-amido-4-methylcoumarin; and N-glutaryl-Gly-Arg 7-amido-4-methylcoumarin.

Suitable diacetylfluorescein derivatives include, for example, fluorescein diacetate, fluorescein di-(β-D-galactopyranoside), and fluorescein dilaurate.

Where the biological activity to be detected is alpha-D-glucosidase, chymotrypsin, suitable fluorogenic enzyme substrates are 4-methylumbelliferyl-alpha-D-glucoside, 7-glutarylphenylalanine-7-amido-4-methyl coumarin, or 4-methylumbelliferyl heptanoate, respectively. Where the biological activity to be detected is alpha-L-arabinofuranosidase, a suitable fluorogenic enzyme substrate is 4-methylumbelliferyl-alpha-L-arabinofuranoside. Where the biological activity to be detected is beta-D-glucosidase, a suitable fluorogenic enzyme substrate is 4-methylumbelliferyl-beta-D-glucoside.

In any of the embodiments of the method, the first and/or second indicator system can comprise a pH indicator dye used in conjunction with a metabolizable nutrient. The pH indicator dye can be selected according to criteria known in the art such as, for example, pH range, compatibility with the indicator and/or target microorganisms, and solubility. In some embodiments, a salt form of the pH indicator may be used, for example, to increase the solubility of the pH indicator in an aqueous mixture. Nonlimiting examples of suitable pH indicator dyes include, for example, thymol blue, tropeolin OO, methyl yellow, methyl orange, bromophenol blue, bromocresol green, methyl red, bromothymol blue, phenol red, neutral red, phenolphthalein, thymolphthalein, alizarin yellow, tropeolin O, nitramine, trinitrobenzoic acid, thymol blue, bromophenol blue, tetrabromophenol blue, bromocresol green, bromocresol purple, methyl red, bromothymol blue, phenol red, Congo red, and cresol red.

The metabolizable nutrient can be any metabolizable nutrient known in the art to react with at least one microorganism (either an indicator microorganism and/or a target microorganism) and to result in a pH change (e.g., a localized pH change) in an aqueous medium that is in fluid contact with the microorganism. The nutrient can be selected from a variety of nutrient types known in the art. Nonlimiting examples of nutrient types include carbohydrates (e.g., sugars, polysaccharides, and derivatives thereof), fats (e.g., fatty acids, fatty acid esters, and derivatives thereof), amines (e.g., amino acids, peptides, oligopeptides, proteins, polyamines, and derivatives thereof), polyphosphates, purines, pyrimidines, nucleosides, and nucleotides.

In some embodiments, the optional second indicator system can be provided in a culture device (e.g., in an agar culture medium in a petri dish; in a dehydrated culture medium in a device such as a Petrifilm culture device, for example). When provided as a component of a hydrogel, such as a component of an agar culture medium, the optional second indicator system is provided in fluid communication with the culture medium. When provided as a dehydrated component as part of a rehydratable culture device, such as a Petrifilm plate, the optional second indicator system is brought into fluid communication with the culture medium, as indicated in step 154 of FIG. 1. This can be accomplished, for example, by rehydrating the dehydrated culture medium in the device with a liquid (e.g., water, a buffer, a diluent). In some embodiments, rehydratable culture media include cold-water-soluble gelling agents such as agar, agarose, guar gum, xanthan gum, locust bean gum, polyvinyl alcohol, and/or polyvinylpyrrolidone, for example. Optionally, the liquid may contain the sample material, thereby permitting the simultaneous performance of step 154 and the inoculation step 156 by the operator.

Inoculating the culture device can be done by a variety of methods that are known in the art. Nonlimiting examples of suitable inoculation methods include pour-plate techniques, surface inoculation techniques, streak-plating techniques, swab-plating techniques, and surface contact-plating techniques (e.g., Rodac plating methods). Filter membrane plating techniques may be used in the present method, provided that the membrane filter does not substantially interfere with the reaction between the microorganisms and the indicator systems or interfere with the observation of the indicator systems.

Methods of the present disclosure include incubating an inoculated culture device for a period of time. A person of ordinary skill in the relevant art will recognize that the incubation temperature may be selected according to the microorganism to be detected. For example, if a yeast or mold is to be detected, the first incubation temperature typically may be from about room temperature (ca. 23° C.) to about 32° C. For example, if a bacterium is to be detected, the first incubation temperature typically may be from about room temperature to about 45° C.

According to the present disclosure, the incubation period may be as short as about one hour. In some embodiments, the first incubation is less than about 4 hours (e.g., less than about 2 hours, less than about 3 hours, or less than about 4 hours. In some embodiments, the incubation period is less than about 8 hours (e.g., less than about 5 hours, less than about 6 hours, less than about 7 hours, or less than about 8 hours). In some embodiments, the incubation is less than about 12 hours (e.g., about 9 hours, about 10 hours, about 11 hours, or about 12 hours. In some embodiments, the incubation period is less than or equal to about 15 hours (e.g., less than about 13 hours, less than about 14 hours, or less than about 15 hours. In some embodiments, the incubation period is up to 48 hours (e.g., less than about 24 hours, less than about 36 hours, or less than about 48 hours.

After the incubation period, the culture device is observed for an indication of the presence of an indicator microorganism. In some embodiments, the culture device is visually observed. In some embodiments, observing the culture device can comprise using an imaging device to observe the culture device. Imaging devices for scanning and, optionally, analyzing a culture device are known in the art and include, for example, PETRIFILM Plate Reader (PPR), available from 3M Company (St. Paul, Minn.), the PETRISCAN Colony Counter available from Spiral Biotech (Norwood, Mass.), and the PROTOCOL and ACOLYTE plate scanners available from Symbiosis (Cambridge, U.K.).

In the embodiments that utilize the optional second indicator system, an indication of the presence of an indicator microorganism can be observed by detecting a conversion of the second indicator system from a first state to a second state. For example, in some embodiments, the second indicator system may include a chromogenic reagent (e.g., triphenyltetrazolium chloride or 5-bromo-4-chloro-3-indolyl-β-D-glucopyranoside) that exists in a colorless first state until it is converted (e.g., by indicator microorganisms) to a colored second state. In other embodiments, the second indicator system may include a fluorogenic reagent (e.g., 4-methylumbelliferyl β-D-galactoside or fluorescein diacetate) that exists in a colorless first state until it is converted (e.g., by indicator microorganisms) to a fluorescent second state. In yet other embodiments, the second indicator system may include a reagent (e.g., a pH indicator) that can be converted from a first colored or fluorescent state to a second colored or fluorescent state by a product of microbial activity (e.g., the fermentation of a carbohydrate to acid end-products).

In some embodiments, detecting a conversion of the second indicator system from a first state to a second state can comprise observing a microorganism colony to detect the conversion. In some embodiments, detecting a conversion of the second indicator system from a first state to a second state can comprise observing the culture medium to detect the conversion.

Figure 2:
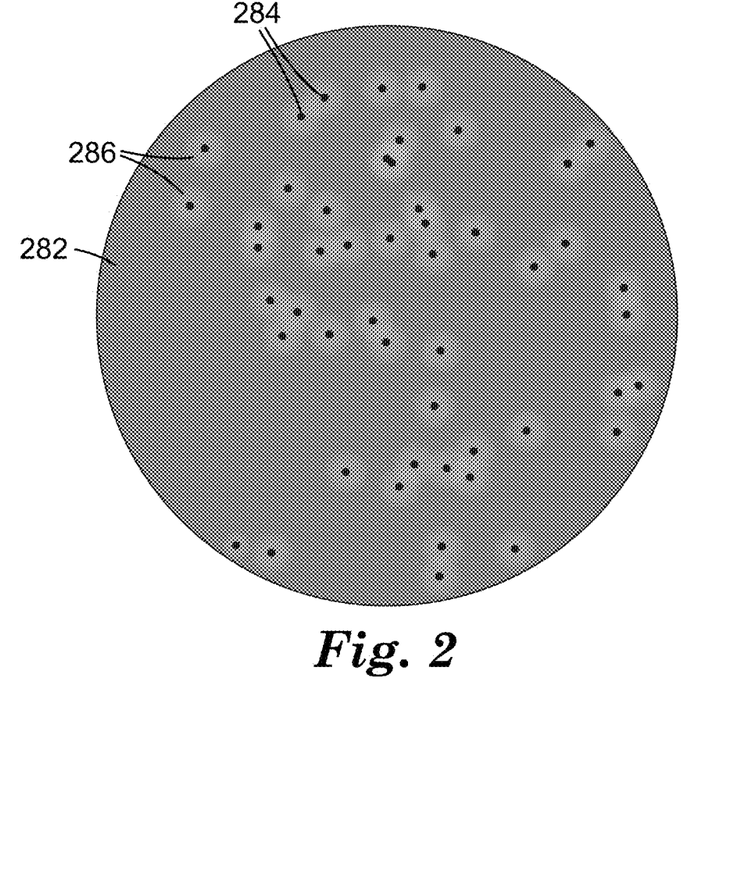
FIG. 2 is a top view of one embodiment of a culture device with colonies of indicator microorganisms disposed therein.

FIG. 2 illustrates several aspects of detecting an indicator microorganism according to the present disclosure. FIG. 2 shows a top view of one embodiment of an inoculated culture device that includes indicator microorganisms reacting with a second indicator system. The culture device has a culture medium 282 that includes a second indicator system that includes a fermentable carbohydrate (e.g., glucose) and a reagent (e.g., chlorophenol red) in a first state (the first state is illustrated as dark gray in FIG. 2; chlorophenol red exists in a violet-colored first state in a culture medium having a pH about 6.8 or higher). Also shown in FIG. 2 are indicator microorganism colonies 284 that have fermented the glucose to diffusible acid end-products, which react with the reagent to convert it to a second state (the second state is illustrated as a light gray halo 286 surrounding the colonies 284 in FIG. 2; chlorophenol red converts to a yellow-colored second state in a culture medium having a pH less than about 5.2). In some embodiments, the colonies may be stained by the reagent and may appear as the same (or a similar) color as the culture medium immediately surrounding them. In other embodiments (not shown), the second indicator system may simply comprise an enzyme substrate or redox reagent that changes from a first state to a second state and thereby directly changing the color or fluorescent properties of the colonies themselves, rather than the culture medium surrounding the colonies.

In the embodiments that do not utilize the optional second indicator system (e.g., a culture device containing a selective agar culture medium, not shown), an indication of the presence of an indicator microorganism can be detected by observing the presence of a bacterial colony (e.g., by its typical size, shape, color, and/or morphology, as known in the art) on or in the culture medium.

Table 1 shows several nonlimiting examples of selective culture media that can be used to support the growth of Enterobacteriaceae microorganisms, an exemplary group of indicator microorganisms that indicate the presence of *Salmonella* target microorganisms. Also shown in Table 1 are exemplary indicator systems (i.e., second indicator systems, according to the present disclosure) that can be used to detect the Enterobacteriaceae microorganisms. Exemplary first indicator systems that can be used to indicate the presence of *Salmonella* target microorganisms include caprylic acid esterase enzyme substrates (disclosed in PCT Patent Application Publication No. WO2007023185, which is incorporated herein by reference in its entirety); 2-deoxy-D-ribose plus neutral red (disclosed in U.S. Pat. No. 7,150,977; which is incorporated herein by reference in its entirety); 5-bromo-4-chloro-3-indolyl-α-D-galactopyranoside (disclosed in U.S. Pat. No. 6,368,817; which is incorporated herein by reference in its entirety); propanediol plus neutral red (disclosed in U.S. Pat. No. 5,194,374; which is incorporated herein by reference in its entirety); and a combination of melibiose, mannitol, sorbitol, and neutral red (disclosed in U.S. Pat. No. 5,786,167; which is incorporated herein by reference in its entirety).

TABLE 1

| Culture Medium | Indicator System |
| --- | --- |
| Violet Red Bile Agar | Glucose + neutral red |
| PETRIFILM Enterobacteriaceae Count Plate | Glucose + chlorophenol red |

An exemplary embodiment of a method of detecting a *Salmonella* target microorganism according to the present disclosure includes using a culture device (e.g., an agar Petri plate or a PETRIFILM culture device) with a culture medium that includes the components listed in Table 2. When preparing the agar culture medium, all of the components except the sodium novobiocin and the cefsulodin are mixed together in any order and thereafter boiled and cooled to form a basal medium. The sodium novobiocin and the cefsulodin are added to the cooled, boiled basal medium just prior to completion of the plating medium. In addition to the culture medium, a detection article is prepared with a first indicator system comprising 5-bromo-4-chloro-3-indolyl-α-D-galactopyranoside, as described in Example 1. The culture medium is inoculated with a sample and incubated for a period of time (e.g., about 18-48 hours). After incubation, the culture device is observed for an indication of the presence of at least one indicator microorganism (e.g., a generally circular, red colony and/or zone that indicates the fermentation of 2-deoxy-D-ribose to an acid end product that changes the neutral red pH indicator from colorless to red). The zone may have a visible colony in or near its center. If an indicator microorganism is detected, the detection article is contacted with the culture medium and the article-contacted culture medium can be incubated for a period of time (e.g., about 1-5 hours) and observed for an indication of the presence of a target microorganism (i.e., a blue-colored colony generally in the center of a red zone that was formed from the reaction of the microorganisms with the first indicator system. Optionally, an additional second indicator system comprising a chromogenic β-galactopyranoside substrate that produces a different color than the 5-bromo-4-chloro-3-indolyl-α-D-galactopyranoside) can be added to the culture medium or the detection article. The additional second indicator system can be used to further identify non-target indicator microorganisms, such as certain strains of E. coli and Citrobacter freundii. As an alternative to neutral red, other pH indicators known in the art can be used in the second indicator system to detect acid end products from the fermentation of the 2-Deoxy-D-ribose. Examples of other suitable pH indicators are disclosed herein. In some embodiments, other second indicator systems (e.g., triphenyltetrazolium chloride) can be used in place of or in addition to the 2-Deoxy-D-ribose/neutral red indicator system to indicate the presence of indicator microorganisms. In some embodiments, other second indicators can be incorporated into the detection article instead of the culture medium. Alternative first indicator systems that could be included in the detection article may include other chromogenic or fluorogenic enzyme substrates for α-galactosidase, chromogenic or fluorogenic enzyme substrates for caprylate esterase, or indicator systems to detect phenylalanine deaminase or propanediol fermentation.

TABLE 2

| Component | Grams/Liter |
| --- | --- |
| Yeast Extract | 3.00 |
| Proteose Peptone | 10.00 |
| Lab Lemco Powder | 1.00 |
| Sodium Chloride | 5.00 |
| L-phenylalanine | 3.50 |
| Ferric Ammonium Citrate | 0.50 |
| Bile Salts #3 | 0.40 |
| Bile Salts | 0.20 |
| 2-deoxy-D-ribose | 12.0 |
| Neutral Red | 0.03 |
| Agar* | 15.97 |
| Deionized water* | 950 mL/liter |

TABLE 2-continued

| Component | Grams/Liter |
| --- | --- |
| Sodium novobiocin | 0.02 |
| Cefsulodin | 0.006 |

Nonlimiting examples of selective culture media that can be used to support the growth of Enterobacteriaceae and/or coliform microorganisms, exemplary groups of indicator microorganisms that indicate the presence of E. coli O157:H7 target microorganisms, include Violet Red Bile-Glucose medium, Violet Red Bile-Lactose medium, PETRIFILM E. coli Count Plates, PETRIFILM Coliform Count plates, PETRIFILM Enterobacteriaceae Count plates, and PETRIFILM Rapid Coliform Count plates. Exemplary first indicator systems that can be used to indicate the presence of E. coli O157:H7 target microorganisms include a combination of salicin, adonitol, inositol, and sorbitol with phenol red (disclosed in U.S. Pat. No. 6,617,149; which is incorporated herein by reference in its entirety).

Nonlimiting examples of selective culture media that can be used to support the growth of Listeria microorganisms, an exemplary group of indicator microorganisms that indicate the presence of Listeria monocytogenes target microorganisms, include Modified Oxfords Medium and R&F medium. Exemplary first indicator systems that can be used to indicate the presence of Listeria monocytogenes target microorganisms include phosphatidylinositol phospholipase C enzyme substrates (disclosed in U.S. Patent Application Publication No. 20070259393, which is incorporated herein by reference in its entirety) and alpha mannosidase enzyme substrates (disclosed in U.S. Pat. No. 7,351,548; which is incorporated herein by reference in its entirety). Non-limiting examples of first indicator systems that can be used to detect Listeria monocytogenes target microorganisms include 5-bromo-4-chloro-3-indoxyl-myo-inositol-1-phosphate, 5-Bromo-6-chloro-3-indoxyl myo-inositol-1-phosphate, ammonium salt, 4-Methylumbelliferyl myo-inositol-1-phosphate, N-methyl-morpholine salt,3-indoxyl-α-D-mannopyranoside, 5-bromo-3-indoxyl-α-D-mannopyranoside, 4-chloro-3-indoxyl-α-D-mannopyranoside, 5-iodo-3-indoxyl-α-D-mannopyranoside, 5-bromo-4-chloro-3-indoxyl-α-D-mannopyranoside, chloro-3-indoxyl-α-D-mannopyranoside, 5-bromo-6-chloro-3-indoxyl-α-D-mannopyranoside, 6-bromo-3-indoxyl-α-D-mannopyranoside, 6-chloro-3-indoxyl-α-D-mannopyranoside, 6-fluoro-3-indoxyl-α-D-mannopyranoside, 4,6-dichloro-3-indoxyl-α-D-mannopyranoside, 6,7-dichloro-3-indoxyl-α-D-mannopyranoside, 4,6,7-trichloro-3-indoxyl-α-D-mannopyranoside, 5-bromo-4-chloro-N-methyl-α-D-mannopyranoside, 3-indoxyl-α-D-mannopyranoside, and N-methyl-3-indoxy-α-D-mannopyranoside, 6-Bromo-2-naphthyl-α-D-mannopyranoside, 4-Methylumbelliferyl-α-D-mannopyranoside, and 4-Nitrophenyl-α-D-mannopyranoside.

In a preferred embodiment, a thin film culture device to detect the presence of a Listeria microorganism can comprise a dehydrated broth medium that includes proteose peptone, tryptone, casamino acids, Lab Lemco Powder/beef extract, glucose, yeast extract, dipotassium hydrogen phosphate, lithium chloride, bovine serum albumin, guar gum, nalidixic acid (sodium salt), chromogenic enzyme substrates to detect b-glucosidase enzyme activity (e.g., Salmon-β-D-glucoside and/or Magenta-β-D glucoside), and ceftazidime pentahydrate. A liquid sample is used to inoculate the medium and a *Listeria* microorganism, if present, grows and forms colonies that are red-colored due to the hydrolysis of the β-glucosidase chromogenic enzyme substrates. If a *Listeria* microorganism is detected in the culture device, the inoculated medium in the culture device optionally can be contacted with a detection article comprising a dehydrated coating that includes a chromogenic indicator to detect phosphatidylinositol phospholipase C enzyme activity (e.g., 5-Bromo-4-chloro-3-indoxyl-myo-inositol-1-phosphate), guar gum and a phosphate buffer. If one or more of the colonies include *Listeria monocytogenes* microorganisms, it will hydrolyse the phosphatidylinositol phospholipase C enzyme substrate, causing the colonies to turn blue. Advantageously, the detection article need only be used if a *Listeria* microorganism is first detected by observing evidence of β-glucosidase enzyme activity associated with a colony.

Nonlimiting examples of selective culture media that can be used to support the growth of Enterobacteriaceae microorganisms, an exemplary indicator microorganism that indicates the presence of *Cronobacter sakazakii* target microorganisms, include Violet Red Bile-Glucose medium and PETRIFILM Enterobacteriaceae Count plates. Exemplary first indicator systems that can be used to indicate the presence of *Cronobacter sakazakii* target microorganisms include chromogenic alpha glucosidase and beta cellobiosidase enzyme substrates (disclosed in U.S. Patent Application Publication No. 2006/0257967 which is incorporated herein by reference in its entirety).

In some embodiments, a group of indicator microorganisms that is known to be found in a similar environment (e.g., fecal material) as the target microorganism may not actually include the target microorganism. An example of this condition is illustrated by the relationship of coliform indicator microorganisms and *Salmonella* target microorganisms. Coliform bacteria are found in fecal material and are characterized by the ability to ferment lactose to acid end products. Certain *Salmonella* target microorganisms (e.g., *Salmonella enterica Typhimurium*) are found in fecal material and do not ferment lactose to acid end products. Thus, a method according to the present disclosure may include providing a first indicator system (e.g., 5-bromo-4-chloro-3-indolyl-α-D-galactopyranoside) to detect *Salmonella* target microorganisms and a second indicator system (e.g., lactose and neutral red) to detect coliform indicator microorganisms. In this embodiment, colonies reacting with the first indicator system would not react with the second indicator system.

The observation of an indication of the presence of an indicator organism connotes the possible presence of a target microorganism (e.g., a potential pathogen) in the sample. Thus, it is a feature of the method that, when an indication of the presence of indicator microorganisms is observed, a detection article can be used to confirm the presence or absence of the target microorganism in the sample. Conversely, in some embodiments where an indication of the presence of indicator microorganisms is not observed in the culture device, the use of a detection article in the method can be avoided because the absence of an indicator microorganism in the sample connotes the absence of a target microorganism in the sample.

Figure 3:
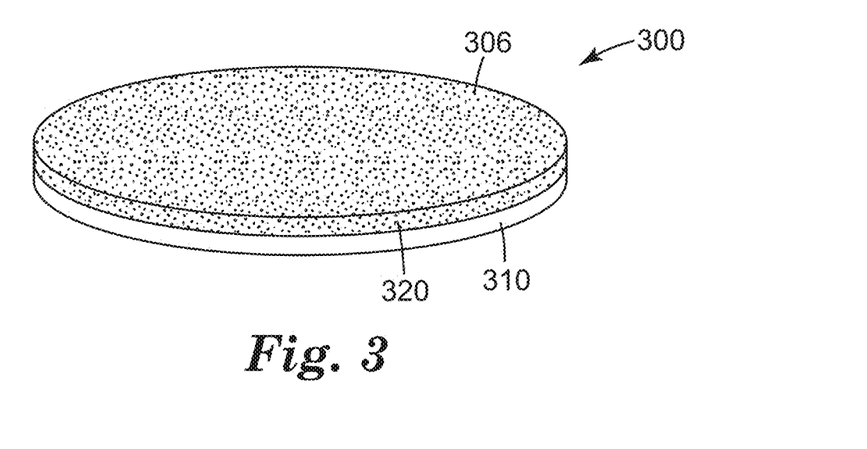
FIG. 3 is a perspective view of one embodiment of a detection article according to the present disclosure.

Methods of the present disclosure comprise providing a detection article comprising a first indicator system. FIG. 3 shows a perspective view of one embodiment of a detection article 300 according to the present disclosure. The detection article 300 comprises a solid support 310 with upper and lower major surfaces and a coating 320 disposed thereon.

The coating 320 comprises a first indicator system, as described herein. The first indicator system can be selected to detect a particular target microorganism. Optionally, an adhesive layer (not shown) may be disposed on the solid support 310 between the solid support 310 and the coating 320. The optional adhesive layer should comprise an adhesive that does not substantially interfere with the reaction of the first indicator system with the target microorganism and/or interfere with the observation of the second indicator system. A nonlimiting example of a suitable adhesive includes the isooctylacrylate/acrylamide (94:6) pressure-sensitive adhesive described in U.S. Pat. No. 4,565,783; which is incorporated herein by reference in its entirety.

In some embodiments, the coating 320 is substantially water-free (i.e., it has a water content no greater than about the water content of the dehydrated coating once it has been allowed to equilibrate with the ambient environment). In some embodiments, the coating 320 can be applied to the substrate 310 or the optional adhesive layer (not shown) as a dry coating such as a powder or the coating can be applied to the substrate as a liquid that is subsequently dried on the substrate, both processes as described, for example, in U.S. Pat. No. 4,565,783. In some embodiments, the article 300 can be constructed, coated, and dried as described for the manufacture of the composite in U.S. Pat. No. 6,022,682, which is incorporated herein by reference in its entirety.

In some embodiments, the coating 320 comprises a binder. There are many binders that would be suitable for use in the detection article 300. Nonlimiting examples of suitable binders include agarose, guar gum, xanthan gum, locust bean gum, and other natural gums. A preferred binder is guar gum.

The coating 320 preferably may also include other constituents such as, for example, a suitable buffering agent to control the pH at a point where a reaction between the first indicator system and the target microorganisms is facilitated. The choice of the particular buffering agent (e.g. a phosphate buffer) and pH (e.g., 7.2) may depend upon the first indicator system and/or the target microorganism, as will be recognized by a person having ordinary skill in the art.

The solid support 310 should be selected from materials that can be coated and that do not substantially obscure the observation of the reactants or products of the first indicator system and, optionally, the second indicator system. The solid support 310 may be a polymer film, such as a polyester film. The solid support 310 may be derived from a sheet material (e.g., polymer film, paper, nonwoven), allowing for cutting, or punching, of detection articles 300 of desired size or shape following coating and drying. In some embodiments, the solid support 310 may be transparent or translucent or it may become transparent or translucent when placed in contact with a hydrogel. The material used for the solid support 310 may be selected to impart any degree of rigidity or flexibility to the detection article 300. In addition, the detection article 300 can be prepared in any shape (e.g., circular, ovoid, square, rectangular, etc.) or thickness, depending on what is desired for a particular application.

The solid support 310 preferably is transparent or at least translucent, to allow the viewing of color changes that develop when the article is placed in fluidic contact with a culture device. The solid support 310 also provides stability to the article and protects it from damage.

The solid support 310 may be selected such that it is peelable from the coating 320, leaving the coating free for use in testing (e.g., in fluidic contact with a culture medium) without the solid support 310. For example, where a polyester film is used as the solid support, the solid support 310 may be peelable from the coating 320 when the coating 320 becomes hydrated after contact with the culture device.

In use, the detection article is brought into fluidic contact with the culture medium of the culture device. Preferably, the detection article and the culture medium will be brought into contact in the culture device (e.g., by placing the detection article in contact with the culture medium in the culture device). In certain preferred embodiments, the detection article is dimensioned so that it has substantially the same shape and surface area so that the article contacts an entire surface of the culture medium in the culture device. In some embodiments, the detection article may be prehydrated (e.g., with sterile water or buffer), although it is contemplated that the moisture in the culture medium is sufficient to hydrate the detection article, thereby permitting the first indicator system to come into fluidic contact with microorganisms present in the culture device.

Without being bound by theory, it is believed that the fluidic contact between the culture medium and the detection article permits the diffusion of the first indicator system, a metabolite produced by the microorganism, and/or the microorganism (or component thereof, such as an enzyme, for example) such that a component of the first indicator system can react with the metabolite, the target microorganism, or a component of the target microorganism and be converted from a first state to a second state. Thus, in some embodiments, the conversion of the first indicator system from a first state to a second state, if present, is indicative of the presence of at least one target microorganism.

In some embodiments, the conversion of the first indicator system from a first state to a second state, if absent, is indicative of the presence of at least one target microorganism. In these embodiments of the method, when an indicator microorganisms changes the first indicator system from a first state to a second state (e.g., the colony and/or the culture medium immediately surrounding the colony becomes colored or fluorescent), then the indicator microorganism is not the target microorganism. Conversely, in these embodiments, if the indicator microorganism does not change the first indicator system from a first state to a second state, it is an indication that the indicator microorganism is the target microorganism. A particular nonlimiting example can illustrate this point. Certain microorganisms of the genus *Shigella* are pathogenic to humans and, thus, *Shigella* is an example of a target microorganism. *Shigella* is a genus of the Enterobacteriaceae family. Because Enterobacteriaceae microorganisms (including *Shigella* species) can be found in fecal material, Enterobacteriaceae microorganisms are an example of indicator microorganisms for *Shigella*. In an embodiment of the method of the present disclosure, a sample of material can be inoculated on selective culture media for Enterobacteriaceae (e.g., violet red bile agar or PETRIFILM Enterobacteriaceae Count Plates). If indicator microorganisms are detected on the culture medium, a detection article comprising, for example, a chromogenic enzyme substrate to detect β-glucosidase, β-fucosidase, and/ or N-acetyl-β-galactosaminidase can be contacted with the culture medium. A conversion of any one of those enzyme substrates from an uncolored state to a colored state is an indication that the colony is not the target microorganism because *Shigella* target microorganisms do not comprise any of the corresponding enzyme activities for those enzyme substrates.

After bringing the detection article into fluidic contact with the culture medium, the article-contacted culture medium is observed to detect a conversion of the first indicator system from a first state to a second state (e.g., from a colorless state to a colored state, from a nonfluorescent state to a fluorescent state, from a first color to a second color). This conversion can be detected, for example, by any of the detection means discussed herein to detect a conversion of the second indicator system from a first state to a second state. Optionally, in some embodiments, the article-contacted culture medium can be incubated at a predetermined temperature for a period of time to facilitate the conversion of the first indicator system from a first state to a second state. The incubation temperature can be, for example, ambient temperature (about 23° C.), up to about 28° C., up to about 30° C., up to about 35° C., up to about 37° C., up to about 42° C., or up to about 45° C. In some embodiments, the article-contacted culture medium can be incubated at the same temperature as the incubation temperature used to grow and detect the indicator microorganisms. In some embodiments, the article-contacted culture medium can be incubated at a different (e.g., lower or higher) temperature than the incubation temperature used to grow and detect the indicator microorganisms.

In some embodiments, the article-contacted culture medium can be incubated for at least about 15 minutes. In some embodiments, the article-contacted culture medium can be incubated for at least about 30 minutes. In some embodiments, the article-contacted culture medium can be incubated for at least about 60 minutes. In some embodiments, the article-contacted culture medium can be incubated for at least about 90 minutes. In some embodiments, the article-contacted culture medium can be incubated for at least about 2 hours. In some embodiments, the article-contacted culture medium can be incubated for at least about 4 hours. In some embodiments, the article-contacted culture medium can be incubated up to about 60 minutes. In some embodiments, the article-contacted culture medium can be incubated up to about 90 minutes. In some embodiments, the article-contacted culture medium can be incubated up to about 2 hours. In some embodiments, the article-contacted culture medium can be incubated up to about 3 hours. In some embodiments, the article-contacted culture medium can be incubated up to about 4 hours. In some embodiments, the article-contacted culture medium can be incubated up to 5 hours. In some embodiments, the article-contacted culture medium can be incubated up to 8 hours. In some embodiments, the article-contacted culture medium can be incubated up to 12 hours. In some embodiments, the article-contacted culture medium can be incubated up to 24 hours. In some embodiments, the article-contacted culture medium can be incubated between about 15 minutes and about 8 hours, inclusive. In some embodiments, the article-contacted culture medium can be incubated between about 30 minutes and about 8 hours, inclusive. In some embodiments, the article-contacted culture medium can be incubated between about 30 minutes and about 5 hours, inclusive. In some embodiments, the article-contacted culture medium can be incubated between about 1 hour and about 5 hours, inclusive. In some embodiments, the article-contacted culture medium can be incubated between about 2 hours and about 5 hours, inclusive. In some embodiments, the article-contacted culture medium can be incubated between about 2 hours and about 4 hours, inclusive.

Figure 4:
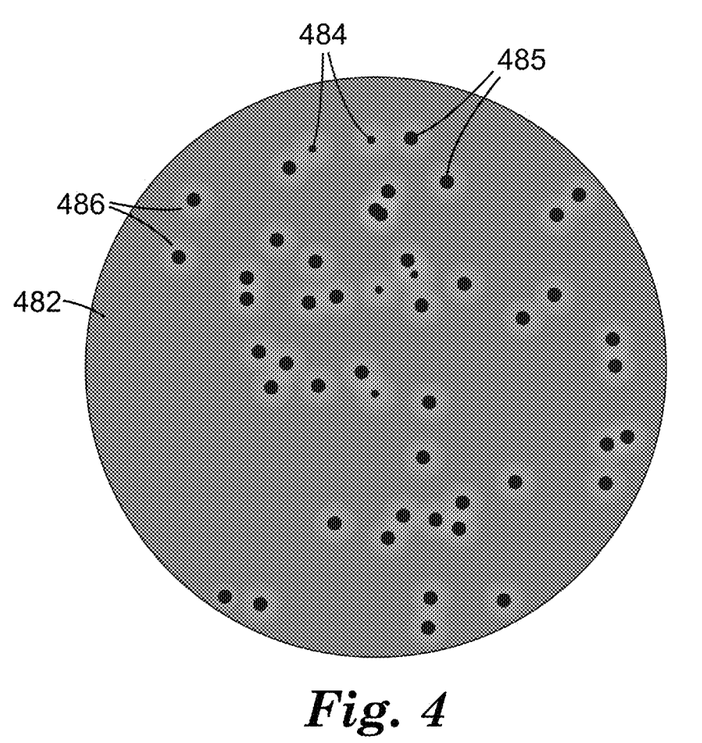
FIG. 4 is a top view of the culture device of FIG. 3 after the placement of a detection article therein.

FIG. 4 shows a top view of the culture device of FIG. 3 after placement of a detection article in contact with the culture (growth) medium in the device. The culture device has a culture medium 482 on and/or in which colonies grow. As shown in FIG. 2, indicator microorganism colonies 484 are present and have changed the first indicator system from a first state (dark gray) to a second state (light gray), forming a distinctive halo 486 around the indicator microorganism colonies 484. Also shown in FIG. 4 are target microorganism colonies 485, which appear larger than the indicator microorganism colonies 484. This can be due, for example, to the conversion of the second indicator system from a first state to a second state. In some embodiments, the second indicator system may be a precipitable chromogenic enzyme substrate (e.g., 5-bromo-4-chloro-3-indolyl-β-D-glucuronide) which, when reacted with a target microorganism, can turn the colony blue and may make the colony appear slightly larger. The target microorganism colonies 485 also have reacted with the first indicator system and have halos 486 surrounding them.

Methods of the present disclosure optionally can further comprise the step of enumerating a type of microorganism. Enumerating a type of microorganism comprises counting a number of colonies (or colony-forming units) of the particular type of microorganism. The number of enumerated colony-forming units can be used to estimate the number of microorganisms per gram (or per milliliter) in the original sample. The number of enumerated colony-forming units can be compared to a specification to determine whether the original sample complies with a quality standard, for example. In some embodiments, all of the microorganisms of a particular type (e.g., indicator microorganisms, target microorganisms) can be enumerated. In some embodiments, a portion (e.g. up to a predetermined threshold number) of the microorganisms of a particular type can be enumerated.

In some embodiments, enumerating a type of microorganisms comprises enumerating the number of indicator microorganisms. In some embodiments, enumerating a type of microorganisms comprises enumerating the number of target microorganisms. In some embodiments, enumerating a type of microorganisms comprises enumerating the number of indicator microorganisms and the number of target microorganisms. In some embodiments, enumerating a type of microorganism can comprise using an imaging device to enumerate the microorganisms.

EMBODIMENTS

Embodiment 1 is a method of detecting the presence or absence of a target microorganism, comprising:
  providing:
    a culture device including a culture medium comprising ingredients selected to facilitate growth of a predetermined indicator microorganism;
    a detection article comprising a first indicator system, the first indicator system selected to detect a target microorganism; and
    a sample;
  inoculating the culture device with the sample;
  incubating the inoculated culture device for a period of time sufficient to permit growth of the indicator microorganisms;
  observing the culture device for an indication of a presence of at least one indicator microorganism;
  contacting the culture medium of the incubated culture device with the detection article; and
  observing the article-contacted culture device to detect a conversion of the first indicator system from a first state to a second state.

Embodiment 2 is method of embodiment 1 wherein the conversion of the first indicator system from a first state to a second state, if present, is indicative of the presence of at least one target microorganism.

Embodiment 3 is the method of embodiment 1, wherein the conversion of the first indicator system from a first state to a second state, if absent, is indicative of the presence of at least one target microorganism.

Embodiment 4 is the method of any one of the preceding embodiments, further comprising providing a second indicator system and placing the second indicator system in fluid communication with the culture medium, wherein observing the culture device for an indication of the presence of at least one indicator microorganism comprises detecting a conversion of the second indicator system from a first state to a second state.

Embodiment 5 is the method of any one of the preceding embodiments, wherein providing the culture device further comprises providing a culture device that comprises a hydrogel or a dry, cold-water-soluble gelling agent.

Embodiment 6 is the method of any one of the preceding embodiments, wherein contacting the culture medium with the detection article is performed only when the indication of the presence of at least one indicator microorganism is observed.

Embodiment 7 is the method of any one of the preceding embodiments, wherein providing a culture device further comprises providing a culture device that includes the second indicator system.

Embodiment 8 is the method of any one of embodiments 1 through 7, wherein providing a culture medium comprises providing a culture medium selected to facilitate growth of an Enterobacteriaceae microorganism, wherein providing a detection article comprises providing a detection article to detect a microorganism of the genus *Salmonella*.

Embodiment 9 is the method of embodiment 8, wherein the first indicator system comprises a reagent to detect α-galactosidase or caprylate esterase enzyme activity.

Embodiment 10 is the method of any one of embodiments 1 through 7, wherein providing a culture medium comprises providing a culture medium selected to facilitate growth of an Enterobacteriaceae microorganism, wherein providing a detection article comprises providing a detection article to detect a microorganism of the genus *Shigella*.

Embodiment 11 is the method of embodiment 10, wherein the first indicator system comprises a reagent to detect β-glucosidase, β-fucosidase, N-acetyl-β-galactosaminidase, or a combination of any two or more of the foregoing enzyme activities.

Embodiment 12 is the method of any one of embodiments 1 through 7, wherein providing a culture medium comprises providing a culture medium selected to facilitate growth of an Enterobacteriaceae microorganism, wherein providing a detection article comprises providing a detection article to detect a microorganism of the genus *Cronobacter*.

Embodiment 13 is the method of embodiment 12, wherein the first indicator system comprises a reagent to detect α-glucosidase and/or β-cellobiosidase enzyme activity.

Embodiment 14 is the method of any one of embodiments 1 through 7, wherein providing a culture medium comprises providing a culture medium selected to facilitate growth of an Enterobacteriaceae microorganism, wherein providing a detection article comprises providing a detection article to detect *Escherichia coli*.

Embodiment 15 is the method of embodiment 14, wherein the first indicator system comprises a reagent to detect β-glucuronidase enzyme activity.

Embodiment 16 is the method of any one of embodiments 1 through 7, wherein providing a culture medium comprises providing a culture medium selected to facilitate growth of a coliform microorganism, wherein providing a detection article comprises providing a detection article to detect *Escherichia coli*.

Embodiment 17 is the method of embodiment 16, wherein the first indicator system comprises a reagent to detect β-glucuronidase enzyme activity.

Embodiment 18 is the method of any one of embodiments 1 through 7, wherein providing a culture medium comprises providing a culture medium selected to facilitate growth of a microorganisms of the *Listeria* genus, wherein providing a detection article comprises providing a detection article to detect *Listeria monocytogenes*.

Embodiment 19 is the method of embodiment 18, wherein the first indicator system comprises a reagent to detect α-mannopyranosidase and/or phosphatidylinositol-specific phospholipase C enzyme activity.

Embodiment 20 is the method of any one of embodiments 1 through 19, wherein observing the culture device or the article-contacted culture device comprises observing the culture device visually.

Embodiment 21 is the method of any one of embodiments 1 through 19, wherein observing the culture device or the article-contacted culture device comprises observing the culture device using an imaging device.

Embodiment 22 is the method of any one of the preceding embodiments, further comprising enumerating indicator microorganism colony-forming units in the culture device.

Embodiment 23 is the method of any one of the preceding embodiments, further comprising enumerating target microorganism colony-forming units in the culture device.

Embodiment 24 is the method of any one of the preceding embodiments, wherein contacting the culture medium with the detection article further comprises contacting the culture medium with the detection article at a predetermined temperature.

Embodiment 25 is a detection article comprising a substrate with upper and lower major surfaces and a coating comprising a first indicator system disposed on at least one of the major surfaces, wherein the first indicator system is converted from a first state to a second state by α-galactopyranoside or caprylate esterase enzyme activity.

Embodiment 26 is the article of embodiment 25, wherein the first indicator system includes an indicator selected from the group consisting of 5-bromo-4-chloro-3-indolyl-α-D-galactopyranoside, 5-bromo-6-chloro-3-indolyl-caprylic acid, 5-bromo-4-chloro-3-indolyl-caprylic acid, and a combination of any two or more of the foregoing indicators.

Embodiment 27 is a detection article comprising a substrate with upper and lower major surfaces and a first indicator system coated on at least one of the major surfaces, wherein the first indicator system is converted from a first state to a second state by β-glucuronidase enzyme activity.

Embodiment 28 is the article of embodiment 27, wherein the first indicator system includes an indicator selected from the group consisting of 5-bromo-4-chloro-3-indolyl-β-D-glucuronic acid, p-nitrophenyl-β-glucuronide, p-nitrophenyl-2,3,4-tri-O-acetyl-β-glucuronic acid methyl ester, phenolphthalein glucuronic acid, phenolphthalein mono-P-glucuronic acid, naphthyl-AS-BI-β-D-glucuronide, 4-methylumbelliferyl β-D-glucuronide, 8-Hydroxyquinoline-beta-D-glucuronic acid, sodium salt, 2-Naphthyl-beta-D-glucuronic acid, sodium salt, 4-Nitrophenyl-beta-D-glucuronic acid, sodium salt, Phenolphthalein-beta-D-glucuronic acid, sodium salt monohydrate. 5-Bromo-4-chloro-3-indoxyl-beta-D-glucuronic acid, cyclohexylammonium salt, 3-Indoxyl-beta-D-glucuronic acid, cyclohexylammonium salt, 3-Indoxyl-beta-D-glucuronic acid, sodium salt. 5-Bromo-6-chloro-3-indoxyl-beta-D-glucuronic acid, cyclohexylammonium salt, 5-Bromo-4-chloro-3-indoxyl-beta-D-glucuronic acid, sodium salt anhydrous, and 5-Bromo-4-chloro-3-indoxyl-beta-D-glucuronic acid, sodium salt trihydrate, and a combination of any two or more of the foregoing indicators.

Embodiment 29 is a detection article comprising a substrate with upper and lower major surfaces and a first indicator system coated on at least one of the major surfaces, wherein the first indicator system is converted from a first state to a second state by α-mannopyranosidase or phosphatidylinositol-specific phospholipase C enzyme activity.

Embodiment 30 is the article of embodiment 29, wherein the first indicator system includes an indicator selected from the group consisting of 5-bromo-4-chloro-3-indoxyl-myo-inositol-1-phosphate, 5-Bromo-6-chloro-3-indoxyl myo-inositol-1-phosphate, ammonium salt, 4-Methylumbelliferyl myo-inositol-1-phosphate, N-methyl-morpholine salt,3-indoxyl-α-D-mannopyranoside, 5-bromo-3-indoxyl-α-D-mannopyranoside, 4-chloro-3-indoxyl-α-D-mannopyranoside, 5-iodo-3-indoxyl-α-D-mannopyranoside, 5-bromo-4-chloro-3-indoxyl-α-D-mannopyranoside, chloro-3-indoxyl-α-D-mannopyranoside, 5-bromo-6-chloro-3-indoxyl-α-D-mannopyranoside, 6-bromo-3-indoxyl-α-D-mannopyranoside, 6-chloro-3-indoxyl-α-D-mannopyranoside, 6-fluoro-3-indoxyl-α-D-mannopyranoside, 4,6-dichloro-3-indoxyl-α-D-mannopyranoside, 6,7-dichloro-3-indoxyl-α-D-mannopyranoside, 4,6,7-trichloro-3-indoxyl-α-D-mannopyranoside, 5-bromo-4-chloro-N-methyl-α-D-mannopyranoside, 3-indoxyl-α-D-mannopyranoside, and N-methyl-3-indoxy-α-D-mannopyranoside, 6-Bromo-2-naphthyl-α-D-mannopyranoside, 4-Methylumbelliferyl-α-D-mannopyranoside, 4-Nitrophenyl-α-D-mannopyranoside and a combination of any two or more of the foregoing indicators.

Embodiment 31 is the article of any one of embodiments 25 through 30, further comprising an adhesive layer, wherein at least a portion of the first indicator system is disposed on or in the adhesive layer.

Embodiment 32 is the article of any one of embodiments 25 through 31, wherein the first indicator system is coated on both major surfaces.

Embodiment 33 is the article of any one of embodiments 25 through 32, wherein the substrate is selected from the group consisting of a polymeric film, paper, a nonwoven, a membrane filter and derivatives of any of the foregoing.

Embodiment 34 is the article of any one of embodiments 25 through 33, wherein the coating comprises a binder.

EXAMPLES

Materials

Potassium Phosphate Monobasic ($KH_2PO_4$)—Mallinckrodt Baker, Inc.; Phillipsburg, N.J.

Potassium Phosphate Dibasic ($K2HPO4$)—AMRESCO; Solon, Ohio

Guar gum—M150 guar MEYPROGAT gum, Meyhall Chemical AG 5-bromo-4-chloro-3-indolyl-α-D-galactopyranoside—BIOSYNTH AG, Rietlistr, Switzerland Polyester film—2.91 mil (0.074 mm) clear polyester film BCIG—5-Bromo-4-Chloro-3-Indolyl-beta-D-glucuronide acid Cyclohexylammonium Salt—BIOSYNTH AG Methyl Glucuronide—1-O-Methyl-beta-D-glucuronic Acid, Sodium Salt—BIOSYNTH AG

Example 1. Preparation of a Detection Article to Detect a *Salmonella* Target Microorganism A coating composition was prepared by adding 13.6 g of potassium phosphate monobasic in 1000 mL of reverse osmosis treated water in a 4 L container and mixing with an air mixer for about 1.5 minutes followed by adding 3.4 g of potassium phosphate dibasic and mixing about 2 minutes. Then 11 g of guar gum was slowly added and mixed for about 5 minutes. The container was covered and heated on a hot plate, while mixing, until the mixture reached 80° C. The container was removed from the hot plate and mixed at room temperature for about 15 minutes, and then refrigerated until the mixture was about 40° C. An indicator suspension was prepared by adding the 5-bromo-4-chloro-3-indolyl-α-D-galactopyranoside to 10 mL of reverse osmosis water and vortexing the mixture to form a uniform suspension. After cooling the coating composition to about 40° C., the indicator suspension was mixed into the coating composition.

The mixture was then removed from the refrigerator and allowed to come to approximately room temperature. The mixture was manually knife coated to a width of about 8 inches (20.32 cm) on a 10 inch (25.4 cm) by 54 inch (137.2 cm) sheet of polyester film to obtain a dry coating weight of about 0.150 grams per 24 square inches (9.69 g/m$^2$, "Disk 1A"). The coating procedure was repeated to provide coated films having dry coating weights of 0.185 g/24 square inches (11.95 g/m$^2$, "Disk 1B"), 0.240 g/24 square inches (15.5 g/m$^2$, "Disk 1C"), and 0.30 g/24 square inches (19.38 g/m$^2$, "Disk 1D"). The coated sheets were dried at an oven set at 230 F (110 C) for 5 to 15 minutes until dry. The coated sheets were stored in plastic bags. The sheets were each cut into 4 inch (10.2 cm) squares and the squares were kept in plastic bags until tested.

Example 2. Detecting a *Salmonella* Target Microorganism with a Detection Article A colony of *Salmonella enterica* Agona ((FSD #140) isolated from an agar streak plate, was inoculated into 5 mL of tryptic soy broth and incubated overnight at 35° C. The overnight culture was diluted in Butterfield's Phosphate Diluent to obtain a suspension having approximately 100 colony-forming units (CFU) per milliliter. Four bacterial culture devices (3M™ Petrifilm™ Enterobacteriaceae Count Plates; 3M Company; St. Paul Minn.) were each inoculated with 1 mL of the bacterial suspension according to the manufacturer's instructions, and incubated at 35° C. for 22-24 hours. The devices were inspected and red colonies (about 1 mm diameter) surrounded by yellow acid zones (approximately 24 mm in diameter). The top film of the culture plate was carefully lifted away from the bottom film to expose the culture medium in the culture plate. Two square disks (Disk1A) were inserted into the plate. The first disk was placed with its coated surface against the culture medium adhered to the bottom film (i.e., facing downward). The second disk was placed on top of the first disk with the second disk's coated side facing away from the bottom film (i.e., facing upward). The top film was carefully lowered (using a "rolling" motion) to bring the culture medium adhered to the top film into contact with the coated side of the second disk. Light finger pressure was applied to the outer surface of the top film of the closed plate to ensure contact between the surfaces of the culture device and the coated surfaces of the disks. The procedure was repeated with Disks 1B, 1C, and 1D. The devices with the disks were incubated at 35° C. and inspected every hour for five hours. Digital images were taken during each inspection. The images showed that, within about 3 hours, all of the colonies on each of the plates turned blue to blue-green due to the hydrolysis of the 5-bromo-4-chloro-3-indolyl-α-D-galactopyranoside by the microorganisms in the colonies.

Example 3. Preparation of a Detection Article to Detect an *E. coli* Target Microorganism A coating composition was prepared according to the procedure of Example 1. A suspension was prepared by dissolving 0.4 g of 1-O-methyl-β-D-glucuronic acid (sodium salt) and 2.0 grams of 5-bromo-4-chloro-3-indoxyl-β-D-glucuronic acid in 50 mL of reverse osmosis treated water in a beaker with constant stirring at room temperatures with a magnetic stir bar. The beaker containing indicator suspension was placed in a refrigerator.

The coating composition was removed from the refrigerator when it had cooled to approximately 40° C. and subsequently was mixed with an air motor mixer until a vortex formed. The indicator suspension was added to the coating composition and mixed for about 20 minutes. The resulting detection medium was then covered and refrigerated until used.

Disks 2A, 2B, 2C, and 2D were prepared and stored according to the procedure described in Example 1 having dry coating weights of 0.150 grams per 24 square inches (9.69 g/m$^2$, "Disk2A"), 0.185 g/24 square inches (11.95 g/m$^2$, "Disk2B"), 0.240 g/24 square inches (15.5 g/m$^2$, "Disk2C"), and 0.30 g/24 square inches (19.38 g/m$^2$, "Disk2D").

Example 4. Detecting an *E. coli* Target Microorganism with a Detection Article An isolated colony of *E. coli* strain (ATCC #51813) was inoculated into 5 mL of tryptic soy broth and incubated 35° C. for 20 hours to provide an overnight culture having a bacterial concentration of approximately 2×10$^9$ cfu/mL. The culture was vortexed and 10 microliters of the culture was added to 99 mL of Butterfields Phosphate Buffer (Dilution1). The suspension was shaken vigorously for about 20 seconds, and 5 microliters of this dilution was added to another 99 mL of Butterfields Phosphate Buffer (Dilution2). This suspension was shaken vigorously for about 20 seconds. Sixteen bacterial culture devices (3M™ Petrifilm™ High-Sensitivity Coliform Count Plate; 3M Company; St. Paul Minn.) were each inoculated with 5 mL of Dilution 2 according to the manufacturer's instructions. Four culture devices were incubated at each of 4 temperatures (32° C., 35° C., 37° C., and 44.5° C., respectively) for 22-24 hours. The culture devices were removed from the incubators and a digital image of each plate was recorded with a digital camera. Each colony had a characteristic appearance (i.e., red colony center about 1 mm in diameter surrounded by a red zone about 2-3 mm in diameter) of a coliform colony on the High-Sensitivity Coliform Count Plate.

Disks of each type (i.e., Disk2A, Disk 2B, Disk 2C, and Disk 2D) were placed as described in Example 2 into separate culture device that had been incubated at each temperature The devices with the disks were then incubated at their respective temperature for 5 hours. A digital image of each culture device was recorded after each hour of the 5-hour incubation period.

After the culture devices containing the disks were incubated, they were observed. Each of the red colonies on all of the plates turned blue after the culture device was contacted with the disk and incubated for 5 hours. Plates that were incubated at a higher temperature with the disks were observed to have blue colonies at an earlier time than the plates that were incubated at lower temperatures. Plates that received detection articles with higher coat weights also were observed to have blue colonies at an earlier time than the plates that received detection articles with lower coat weights.

Example 5. Prophetic Example of the Preparation of a Culture Device for Growing *Listeria* Indicator Microorganisms A culture medium composition is prepared with the materials in Table 3. The Proteose Peptone, Tryptone, Casamino acids, and Yeast Extract can be obtained, for example, from Becton Dickinson (Sparks, Md.). The Lab Lemco Powder/Beef Extract can be obtained, for example, from Oxoid (Hampshire, UK). Bovine serum albumin can be obtained from, for example, from Serologicals Corporation (Norcross, Ga.). Beta-D-glucoside indicators can be obtained from BioSynth AG, for example. Ceftazidime can be obtained from Glaxo Wellcome, for example.

TABLE 3

| Component | Material | Grams |
| --- | --- | --- |
| 1 | Proteose peptone | 6.0 |
| 2 | Tryptone | 19.2 |
| 3 | Casamino acids | 12.0 |
| 4 | Lab Lemco Powder/Beef Extract | 10.0 |
| 5 | Glucose | 5.0 |
| 6 | Yeast extract | 14.0 |
| 7 | Potassium phosphate, dibasic | 9.0 |
| 8 | Lithium chloride | 15.0 |
| 9 | Bovine serum albumin | 6.0 |
| 10 | Guar gum | 10 |
| 11 | Nalidixic acid, sodium salt | 0.02 |
| 12 | Salmon-beta-D glucoside | 0.06 |
| 13 | Magenta-beta-D glucoside | 0.066 |
| 14 | Ceftazidime pentahydrate | 0.027 |

A first mixture is prepared by adding components 1-10 (shown in Table 3) to 1000 mL of reverse-osmosis water, mixing to obtain a uniform suspension, heating the mixture until it reaches 80° C. and then cooling to room temperature. While the first mixture is cooling, a second mixture is prepared by mixing the components 11-14 (shown in Table 1 in 10 milliliters of reverse osmosis water. The second mixture is vortexed to provide a uniform mixture, which is added to the first mixture, and then mixed further to provide a uniform culture medium. The culture medium is then refrigerated for 18-24 h (2-8° C.).

The refrigerated culture medium is allowed to warm to room temperature and then knife coated onto a sheet of 2.6 mil (0.074 mm) thick clear polyester film and dried at about 200° F. for 5 to 10 minutes. The knife gap is adjusted to provide a dry coating weight of approximately 515-540 mg/24 in$^2$ (33.27-34.88 g/m$^2$). An 18 mil (0.46 mm) thick sheet of closed cell polystyrene foam is laminated to a pressure-sensitive adhesive transfer tape. Circular openings 2 inches in diameter are die punched from the foam sheet and the foam sheet is laminated to the culture medium-coated side of the polyester film to form a structure similar to the bottom portion of the culture device shown in FIG. 1 of U.S. Pat. No. 4,565,783. The preparation of the culture device is completed by removing the top film from a 3M™ Petrifilm™ Staph Express Count Plate and affixing it to the Styrofoam sheet with double coated adhesive tape, thereby producing a device that resembles the complete culture device shown in FIG. 1 of U.S. Pat. No. 4,565,783.

Example 6. Prophetic Example of the Preparation of a Detection Article to Detect a *Listeria monocytogenes* Target Microorganism A coating composition is made by mixing the guar gum, disodium phosphate, and potassium hydrogen phosphate (shown in Table 4) in 1000 milliliters of reverse osmosis water to form a uniform dispersion as described in Example 1.

TABLE 4

| Material | Grams |
| --- | --- |
| 5-Bromo-4-chloro-3-indoxyl-myo-inositol-1-phosphate | 0.60 |
| Guar gum | 10 |
| Sodium phosphate, dibasic | 8.0 |
| Potassium phosphate, monobasic | 4.0 |

The container with the coating composition is covered and the dispersion is mixed continuously while heated to a temperature of 80° C. Then it is removed from the heat and mixed continuously at room temperature. An indicator suspension is prepared by adding the 5-bromo-4-chloro-3-indoxyl-myo-inositol-1-phosphate (which can be obtained from Biosynth AG, for example) to 10 mL of reverse osmosis water and vortexing to form a uniform suspension. After the coating composition cools to room temperature, the indicator suspension is mixed into the coating composition. The mixture is covered and refrigerated 18-22 hours. The coating mixture is removed from the refrigerator and allowed to warm to about room temperature. A 2.9 mil (0.074 mm) polyester film is knife coated with the mixture according to the procedure described in Example 1 to obtain a film with a dry coating weight of about 80-95 mg/24 in$^2$ (5.17-6.14 g/m$^2$). The polyester film is turned over and knife-coated on the other side in the same manner. The film, coated on both sides is then die-cut into circular disks having a diameter of about 2 inches.

Example 7—Prophetic Example of Detecting a *Listeria monocytogenes* Target Microorganism Enrichment cultures are prepared from food and environmental samples using standard sample-collecting and enrichment broth procedures, (e.g., as specified by the US Department of Agriculture, the Food Safety Inspection Service, or the Bacteriological Analytical Manual). Eight serial, 10-fold dilutions of the culture are prepared in Butterfield's diluent. One milliliter of each dilution is inoculated into individual culture devices described in Example 5. The devices are then incubated 35-37° C. for 18-30 hours. The devices are inspected for typical colony morphology (e.g., red colonies approximately 0.5 to 1.5 mm in diameter) indicative of *Listeria* (an indicator microorganism group that indicates the presence of *Listeria monocytogenes*). If typically colored colonies are seen in the culture device after incubation, the user can further insert a detection article to detect differentiate the colonies. The top film of the culture device is gently pulled back and a 2 inch detection article described in Example 6 is placed into contact with the culture medium. The top film is re-closed, bringing it into contact with the detection article. The top film can be pressed with light finger pressure to contact the growth areas of the device with the detection article. The device is incubated for up to 5 hours at 35-37° C. and inspected periodically (e.g., hourly) for the presence of blue to blue-green color in the colonies. The blue to blue-green-colored colonies indicate the presence of L. monocytogenes.

Example 8—Method of Detecting a Listeria monocytogenes Target Microorganism

Preparation of Thin Film Culture Device—Broth-Coated Substrate:

All of the ingredients shown in Table 5 except the guar gum were mixed with 970 milliliters of deionized water in stainless steel beaker. While mixing, the guar was added and the complete mixture was heated to 80° C. The heated complete mixture was stirred for about 15 minutes, covered, and cooled in a refrigerator overnight. Prior to coating, twenty milliliters of Supplement A (bovine serum albumin, 3.2 g/20 mL) and ten milliliters of Supplement B (ceftazidime pentahydrate, 40 mg/10 mL) were mixed with the coating mixture. The coating mixture with supplements was knife-coated onto clear polyester film (2.91 mil (0.07 mm) thick) using a 15 mil (0.38 mm) gap. The coated polyester was dried for about 8 minutes in an oven set at 210° C. The final coating weight of the dried coated mixture was 0.308 g/24 in$^2$ (0.308 g/154.8 cm$^2$). Styrofoam spacers (20 mil (0.51 mm) thick), with 2-inch (5.08 cm) diameter openings, were adhered to the coated, dried film, as described in Example 1 of U.S. Pat. No. 5,601,998; which is incorporated herein by reference in its entirety. The substrate was cut into approximately 4" (10.2 cm) by 4" (10.2 cm) pieces, each piece having a spacer with the 5-cm opening that framed a circular area of the dried, coated broth composition.

TABLE 5

Composition of coating mixture.

| Component | Material | Grams |
|---|---|---|
| 1 | Proteose peptone No. 3 | 3.127 |
| 2 | Casein peptone type III | 9.6 |
| 3 | Casamino acids | 6.0 |
| 4 | Meat peptone (porcine) | 5.0 |
| 5 | Glucose | 2.5 |
| 6 | Yeast extract | 7.0 |
| 7 | Potassium phosphate, dibasic | 4.5 |
| 8 | Lithium chloride | 9.0 |
| 10 | Guar gum | 12 |
| 11 | Nalidixic acid, sodium salt | 0.01 |

Preparation of Thin Film Culture Device—Powder-Coated Substrate:

Polyethylene-coated paper (0.13 mm thick) was obtained from Schoeller Paper (Pulaski, N.Y.). 6-Chloro-3-indoxyl-β-D-glucopyranoside (X-gluc, part number B5020) was obtained from Biosynth AG (Staad, Switzerland). The X-gluc (139.1 mg was thoroughly mixed into 200 grams of adhesive (a copolymer of isooctylacrylate and acrylamide in a 96:4 weight ratio). The adhesive mixture was then knife-coated onto the polyethylene-coated paper and heated at in an oven at 210° C. to achieve a dry coating weight of 0.237 g/24 in$^2$ (0.237 g/154.8 cm$^2$). The adhesive-coated film was coated with a layer of guar gum that was previously disinfected using ethylene oxide. The excess guar gum was shaken off and the powder-coated substrate was cut into approximately 4" (10.2 cm) by 4" (10.2 cm) pieces.

Assembly of the Thin Film Culture Devices:

A piece of double-stick tape (3M Company, St. Paul, Minn.) was applied along one edge of the Styrofoam spacer on each broth-coated substrate. A powder-coated substrate was aligned (with the powder-coated side facing the spacer) to superimpose the broth-coated substrate and the powder-coated side was adhered to the double-stick tape to form the assembled culture devices.

Preparation of Detection Articles:

A coating mixture was prepared by blending into 1000 milliliters of deionized water the following components: 13.0 grams of guar gum and a solution of 141.3 milligrams of 5-bromo-4-chloro-3-indoxyl-β-myo-inositol-1-phosphate (X-IP, part number B7404-P00, obtained from Biosynth AG) dissolved in 2.0 mL dimethylsulfoxide (DMSO). The mixture was heated in a covered beaker to 80° C. while mixing, mixed at that temperature for an additional 15 minutes, and then cooled in a refrigerator. The mixture was warmed to room temperature before coating. The mixture was knife-coated (25-mil (0.64 mm) gap) onto the clear polyester film described above. The coated film was dried in an oven at 210° C. to achieve a dry coating weight of 0.092 g/24 in$^2$ (0.092 g/154.8 cm$^2$). The coated substrate was cut into approximately 4" (10.2 cm) by 4" (10.2 cm) pieces.

Detection Method.

A pure colony of each of the bacteria shown in Table 6 was inoculated into separate tubes of tryptic soy broth containing yeast extract (TSBYE). The tubes were incubated at 35° C. for 18-24 hours. Individual culture devices (prepared as described in this Example) were opened and hydrated by pipetting 1.5 mL of Butterfield's buffer into the circular area of dehydrated broth defined by the Styrofoam spacer. The culture devices were closed, bringing the powder-coated paper into contact with the buffer and spreading the buffer over the entire circular growth area defined by the spacer. The hydrated plates were allowed to sit at room temperature for 1 hour.

Ten microliters of each overnight Listeria culture were inoculated by streak-plate technique into individual hydrated culture devices and the inoculated culture devices were incubated at 35° C. in a zipper-seal plastic bag for 24 hours. After incubation, the colonies were observed and the colony appearance is described in Table 6.

The incubated plates were opened, causing the hydrated gel containing the bacterial colonies to remain attached to the polypropylene-coated paper substrate. A detection article (described in this Example) was placed in the culture device such that the coated side of the detection article faced the hydrated gel containing the colonies. The culture device was then closed, causing the coated side of the detection article to contact the hydrated gel containing the bacterial colonies. The culture devices were then incubated at 35° C. and observed. The observations are reported in Table 6. The results indicate that only the Listeria monocytogenes microorganisms reacted with (i.e., hydrolyzed) the enzyme substrate indicator (5-bromo-4-chloro-3-indoxyl-β-myo-inositol-1-phosphate) from the detection article.

TABLE 6

Observations of culture devices containing *Listeria* microorganisms.

| Microorganism | Colony Appearance in Culture Device[1] | Colony Appearance after Adding Detection Article[2] |
| --- | --- | --- |
| *Listeria monocytogenes*, ATCC 19111 | Reddish-colored | Blue-colored |
| *Listeria grayi*, ATCC 19120 | Reddish-colored | Reddish-colored |
| *Listeria ivanovii*, ATCC 19119 | Reddish-colored | Reddish-colored |
| *Listeria seeligeri*, ATCC 35967 | Reddish-colored | Reddish-colored |
| *Listeria welshimeri*, ATCC 35897 | Reddish-colored | Reddish-colored |
| *Listeria innocua* | Reddish-colored | Reddish-colored |

[1]Colony appearance after 24 hour incubation
[2]Colony appearance within 15-60 minutes after detection article was contacted with the growth area of the culture device.

Various modifications may be made without departing from the spirit and scope of the invention. These and other embodiments are within the scope of the following claims.

The invention claimed is:

1. A method of detecting a *Shigella* or *Cronobacter* microorganism, comprising the steps of:
 (a) providing:
  (i) a culture device including a culture medium comprising ingredients selected to facilitate growth of an Enterobacteriaceae microorganism;
  (ii) a detection article comprising a first indicator system, the first indicator system selected to detect the *Shigella* or *Cronobacter* microorganism;
   wherein the *Shigella* or *Cronobacter* microorganism is detected by its ability to convert the first indicator system from a first state to a second state; and
  (iii) a sample;
 (b) inoculating the culture device with the sample;
 (c) incubating the inoculated culture device for a period of time sufficient to permit growth of indicator microorganisms;
 (d) observing the culture device for an indication of a presence of at least one indicator microorganism;
 (e) contacting the culture medium of the incubated culture device with the first indicator system of the detection article; and
 observing the article-contacted culture device to detect a conversion of the first indicator system from a first state to a second state, wherein the conversion of the first indicator system from the first state to the second state is indicative of the presence of at least one *Shigella* or *Cronobacter* microorganism.

2. The method of claim 1, wherein the genus is *Shigella* and the first indicator system comprises a reagent to detect β-glucosidase, β-fucosidase, N-acetyl-β-galactosaminidase, or a combination of any two or more of the foregoing enzyme activities.

3. The method of claim 1, wherein the genus is *Cronobacter* and the first indicator system comprises a reagent to detect α-glucosidase activity, β-cellobiosidase enzyme activity, or both.

4. The method of claim 1, wherein providing the culture device further comprises providing a culture device that comprises a hydrogel or a dry, cold water-soluble gelling agent.

5. The method of claim 1, wherein observing the culture device or the article-contacted culture device comprises visual observation.

6. The method of claim 1, wherein observing the culture device or the article-contacted culture device comprises observation using an imaging device.

7. The method of claim 1, wherein contacting the culture medium with the detection article further comprises contacting the culture medium with the detection article at a predetermined temperature.

8. The method of claim 1, further comprising enumerating *Shigella* microorganisms in the culture device.

9. The method of claim 1, further comprising enumerating *Cronobacter* microorganisms in the culture device.

10. The method of claim 1, wherein the detection article comprises a substrate with upper and lower major surfaces and a coating comprising the first indicator system disposed on at least one of the major surfaces.

11. The method of claim 10, wherein the first indicator system is coated on both major surfaces.

12. The method of claim 10, wherein the substrate is selected from the group consisting of a polymeric film, paper, a nonwoven, a membrane filter and derivatives of any of the foregoing.

13. The method of claim 11, wherein the coating comprises a binder.

* * * * *